(12) United States Patent
Ford et al.

(45) Date of Patent: *Apr. 4, 2006
(10) Patent No.: US 7,024,236 B2

(54) FORMULATION AND MANIPULATION OF DATABASES OF ANALYTE AND ASSOCIATED VALUES

(75) Inventors: Russell Ford, Portola Valley, CA (US); Matthew J. Lesho, San Mateo, CA (US); Russell O. Potts, San Francisco, CA (US); Michael J. Tierney, San Jose, CA (US); Charles W. Wei, Fremont, CA (US)

(73) Assignee: Animas Technologies LLC, West Chester, PA (US)

( * ) Notice: Subject to any disclaimer, the term of this patent is extended or adjusted under 35 U.S.C. 154(b) by 28 days.

This patent is subject to a terminal disclaimer.

(21) Appl. No.: 10/821,055

(22) Filed: Apr. 8, 2004

(65) Prior Publication Data

US 2005/0010093 A1 Jan. 13, 2005

Related U.S. Application Data

(63) Continuation of application No. 10/460,557, filed on Jun. 12, 2003, which is a continuation of application No. 09/927,583, filed on Aug. 10, 2001, now Pat. No. 6,633,772.
(60) Provisional application No. 60/226,205, filed on Aug. 18, 2000.

(51) Int. Cl.
*A61B 5/00* (2006.01)

(52) U.S. Cl. .................. 600/345; 600/347; 600/365; 600/300; 707/104.1
(58) Field of Classification Search ......... 600/345–350, 600/365; 707/104.1
See application file for complete search history.

(56) References Cited

U.S. PATENT DOCUMENTS

| 4,703,756 A | 11/1987 | Gough et al. |
| 4,803,625 A | 2/1989 | Fu et al. |

(Continued)

FOREIGN PATENT DOCUMENTS

| EP | 0 483 595 A | 5/1992 |
| WO | WO 96/00109 | 1/1996 |

(Continued)

OTHER PUBLICATIONS

Bolinder et al., "Self–Monitoring of Blood Glucose in Type 1 Diabetic Patients: Comparison with Continuous Microdialysis Measurements of Glucose in Subcutaneous Adipose Tissue During Ordinary Life Conditions," *Diabetes Care* 20(1):64–70 (1997).

(Continued)

*Primary Examiner*—Robert L. Nasser
(74) *Attorney, Agent, or Firm*—RatnerPrestia

(57) ABSTRACT

The present invention relates to methods of formulating analyte data databases, the databases themselves, and methods of manipulating the same. In one aspect the present invention includes the formulation of analyte data points, derived data, and data attributes databases comprising data points collected using an analyte monitoring device capable of frequent monitoring of analyte concentrations or amounts. Such data points may comprise acquired data (e.g., values corresponding to analyte concentrations or amounts as measured by said analyte monitoring device). These data points are then associated with one or more relevant data attributes. The resulting databases may be manipulated to determine relationships among the components of the database.

51 Claims, 9 Drawing Sheets

U.S. PATENT DOCUMENTS

| | | |
|---|---|---|
| 5,247,666 A | 9/1993 | Buckwold |
| 5,251,126 A | 10/1993 | Kahn et al. |
| 5,279,543 A | 1/1994 | Glikfeld et al. |
| 5,362,307 A | 11/1994 | Guy et al. |
| 5,458,140 A | 10/1995 | Eppstein et al. |
| 5,462,051 A | 10/1995 | Oka et al. |
| 5,507,288 A | 4/1996 | Böcker et al. |
| 5,569,186 A | 10/1996 | Lord et al. |
| 5,730,714 A | 3/1998 | Guy et al. |
| 5,735,273 A | 4/1998 | Kurnik et al. |
| 5,747,806 A | 5/1998 | Khalil et al. |
| 5,771,890 A | 6/1998 | Tamada |
| 5,822,715 A | 10/1998 | Worthington et al. |
| 5,827,183 A | 10/1998 | Kurnik et al. |
| 5,914,701 A | 6/1999 | Gersheneld et al. |
| 5,954,685 A | 9/1999 | Tierney |
| 5,960,403 A | 9/1999 | Brown |
| 5,989,408 A | 11/1999 | Baerts et al. |
| 6,023,629 A | 2/2000 | Tamada |
| 6,024,699 A | 2/2000 | Surwit et al. |
| 6,139,718 A | 10/2000 | Kurnik et al. |
| 6,141,573 A | 10/2000 | Kurnik et al. |
| 6,144,869 A | 11/2000 | Berner et al. |
| 6,180,416 B1 | 1/2001 | Kurnik et al. |
| 6,201,979 B1 | 3/2001 | Kurnik et al. |
| 6,233,471 B1 | 5/2001 | Berner et al. |
| 6,272,364 B1 | 8/2001 | Kurnik |
| 6,277,071 B1 | 8/2001 | Hennessy et al. |
| 6,278,999 B1 | 8/2001 | Knapp |
| 6,284,126 B1 | 9/2001 | Kurnik et al. |
| 6,298,254 B1 | 10/2001 | Tamada |
| 6,299,578 B1 | 10/2001 | Kurnik et al. |
| 6,309,351 B1 | 10/2001 | Kurnik et al. |
| 6,326,160 B1 | 12/2001 | Dunn et al. |
| 2003/0208454 A1 * | 11/2003 | Rienhoff et al. ............... 707/1 |
| 2004/0267568 A1 * | 12/2004 | Chandler et al. .............. 705/2 |

FOREIGN PATENT DOCUMENTS

| | | |
|---|---|---|
| WO | WO 97/02811 | 1/1997 |
| WO | WO 99/58190 | 11/1999 |
| WO | WO 00/07013 A | 2/2000 |
| WO | WO 00/47109 A | 8/2000 |

OTHER PUBLICATIONS

Newman et al., "Catalytic Materials, Membranes, and Fabrication Technologies Suitable for the Construction of Amperometric Biosensors," *Analytical Chemistry* 67:4594–4599 (1995).

Ohkubo et al., "Intensive Insulin Therapy Prevents the Progression of Diabetic Microvascular Complications in Japanese patients with Non–Insulin–Dependent Diabetes Mellitus: a Randomized Prospective 6–year Study," *Diabetes Research & Clinical Practice* 28:103–117 (1995).

Tamada et al., "Noninvasive Glucose Monitoring," *JAMA* 282:1839–1844 (1999).

UK Prospective Diabetes Study (UKPDS) Group., "Effect of Intensive Blood–Glucose Control With Metformin on Complications in Overweight Patients with Type 2 Diabetes (UKPDS 34)," *Lancet* 352:837–853 (1998).

Updike et al., "The Enzyme Electrode," *Nature* 214:986–988 (1967).

\* cited by examiner

| mlog record # | record status | log entry type | record type | date | time | sequence number | NOT USED | temperature (internal thermister) | elapsed time | ionto voltage | ionto current | sensor A current | sensor A elapsed biosensor time | sensor B current | sensor B elapsed biosensor time | Sweat Reading |
|---|---|---|---|---|---|---|---|---|---|---|---|---|---|---|---|---|
| | OK or CORRUPT | 1 (IONTO), 2 (MBIO), 3 (ID/ERROR #), 4 (SWEAT) | SHUTDOWN, NEWBAT, START, MBIO, MION, SWEAT | | | 0-47 | | 17-32.4 C | | | | | | | | |
| 0 | OK | 3 | SHUTDOWN | 4/25/00 | 11:54:11 | 32 | 20.2 | 42.5 | 0:00:00 | | | | | | | |
| 1 | OK | 3 | NEWBAT | 4/25/00 | 12:56:16 | 32 | 20.2 | 22.8 | 0:00:00 | | | | | | | |
| 2 | OK | 3 | START | 4/26/00 | 13:28:41 | 32 | 20.2 | 27.1 | 0:00:00 | | | | | | | |
| 3 | OK | 2 | MBIO | 4/26/00 | 13:29:41 | 34 | 20.4 | 28.1 | | | | | | | | |
| 4 | OK | 1 | MION | 4/26/00 | 13:30:41 | 34 | 20.4 | 28.6 | | | | | | | | |
| 5 | OK | 2 | MBIO | 4/26/00 | 13:30:46 | 34 | 20.4 | 28 | 0:02:06 | -2.2 | 0.02 | 3544 | 58 | 3612 | 58 | |
| 6 | OK | 1 | MION | 4/26/00 | 13:31:46 | 34 | 20.4 | 28.4 | 0:03:06 | -3.2 | 0.02 | 2477 | 118 | 2532 | 118 | |
| 7 | OK | 2 | MBIO | 4/26/00 | 13:32:41 | 34 | 20.4 | 28.7 | 0:04:01 | -3.2 | 0.02 | | | | | |
| 8 | OK | 2 | MBIO | 4/26/00 | 13:34:41 | 42 | 21.2 | 29.8 | | | | | | | | |
| 9 | OK | 2 | MBIO | 4/26/00 | 13:36:41 | 42 | 21.2 | 30.4 | | | | | | | | |
| 10 | OK | 2 | MBIO | 4/26/00 | 13:38:41 | 42 | 21.2 | 30.7 | | | | | | | | |
| 11 | OK | 2 | MBIO | 4/26/00 | 13:40:41 | 42 | 21.2 | 31 | | | | | | | | |
| 12 | OK | 2 | MBIO | 4/26/00 | 13:42:41 | 42 | 21.2 | 31.2 | 0:15:29 | 8.9 | 0.16 | 3803 | 359 | 4028 | 359 | |
| 13 | OK | 1 | MION | 4/26/00 | 13:44:09 | 42 | 21.2 | 30.7 | 0:16:56 | 9.7 | 0.32 | 3358 | 479 | 3565 | 479 | |
| 14 | OK | 2 | MBIO | 4/26/00 | 13:45:36 | 42 | 21.2 | 30.9 | | | | 3054 | 599 | 3256 | 599 | |
| 15 | OK | 2 | MBIO | 4/26/00 | 13:49:41 | 42 | 21.2 | 31.7 | | | | | | | | |
| 16 | OK | 2 | MBIO | 4/26/00 | 13:53:41 | 42 | 21.2 | 31.8 | 0:25:18 | -10.7 | 0.32 | 245 | 239 | 231 | 239 | |
| 17 | OK | 1 | MION | 4/26/00 | 13:53:58 | 42 | 21.2 | 31.2 | 0:28:01 | -7.2 | 0.32 | 217 | 479 | 216 | 479 | |
| 18 | OK | 2 | MBIO | 4/26/00 | 13:56:41 | 42 | 21.2 | 31.6 | | | | 259 | 119 | 328 | 119 | |
| 19 | OK | 2 | MBIO | 4/26/00 | 13:58:41 | 42 | 21.2 | 32.2 | | | | 236 | 239 | 275 | 239 | |
| 20 | OK | 2 | MBIO | 4/26/00 | 14:00:41 | 42 | 21.2 | 32.2 | | | | 216 | 359 | 246 | 359 | |
| 21 | OK | 2 | MBIO | 4/26/00 | 14:02:41 | 42 | 21.2 | 32 | | | | 212 | 399 | 242 | 399 | |
| 22 | OK | 2 | MBIO | 4/26/00 | 14:03:21 | 42 | 21.2 | 31.9 | 0:35:01 | 9 | 0.32 | 212 | 404 | 241 | 404 | |
| 23 | OK | 2 | MBIO | 4/26/00 | 14:03:26 | 35 | 20.5 | 31.9 | 0:35:17 | 7 | 0.32 | | | | | |
| 24 | OK | 4 | SWEAT | 4/26/00 | 14:03:57 | 33 | 20.3 | 31.7 | 0:37:56 | | | | | | | 0.41485 |
| 25 | OK | 1 | MION | 4/26/00 | 14:06:36 | 35 | 20.5 | 31.2 | 0:38:01 | | | | | | | |
| 26 | OK | 2 | MBIO | 4/26/00 | 14:06:41 | 33 | 20.3 | 31.6 | | | | | | | | |
| 27 | OK | 4 | SWEAT | 4/26/00 | 14:06:51 | 33 | 20.3 | 31.9 | | | | | | | | 0.29774 |
| 28 | OK | 1 | MION | 4/26/00 | 14:06:56 | 33 | 20.3 | 32.1 | | | | 879 | 9 | 728 | 9 | |
| 29 | OK | 2 | MBIO | 4/26/00 | 14:07:01 | 33 | 20.3 | 32.1 | | | | 664 | 14 | 551 | 14 | |
| 30 | OK | 2 | MBIO | 4/26/00 | 14:07:11 | 33 | 20.3 | 32.1 | | | | 563 | 19 | 465 | 19 | |
| 31 | OK | 2 | MBIO | 4/26/00 | 14:07:21 | 33 | 20.3 | 32.2 | | | | 464 | 29 | 383 | 29 | |
| 32 | OK | 2 | MBIO | 4/26/00 | 14:07:21 | 33 | 20.3 | 32.2 | | | | 415 | 39 | 338 | 39 | |

| mlog record # | record status | log entry type | record type | date | time | sequence number | NOT USED | temperature (internal thermistor) | elapsed time | ionto voltage | ionto current | sensor A current | sensor A elapsed biosensor time | sensor B current | sensor B elapsed biosensor time | Sweat Reading |
|---|---|---|---|---|---|---|---|---|---|---|---|---|---|---|---|---|
| | OK or CORRUPT | (IONTO), 2 (MBIO), 3 (ID/ERROR), 4 (SWEAT) | SHUTDOWN, NEWBAT, START, MBIO, ION, SWEAT | | | 0-47 | | 17-32.4 C | | | | | | | | |
| 384 | OK | 4 | SWEAT | 4/26/00 | 17:23:41 | 35 | 20.5 | 32.5 | 3:55:01 | | | | | | | 0.14579 |
| 385 | OK | 1 | MION | 4/26/00 | 17:23:57 | 33 | 20.3 | 32.1 | 3:55:17 | 4.5 | 0.32 | | | | | |
| 386 | OK | 1 | MION | 4/26/00 | 17:26:36 | 33 | 20.3 | 31.7 | 3:57:56 | 5.6 | 0.32 | | | | | |
| 387 | OK | 4 | SWEAT | 4/26/00 | 17:26:41 | 33 | 20.5 | 32 | 3:58:01 | | | | | | | 0.09001 |
| 388 | OK | 2 | MBIO | 4/26/00 | 17:26:51 | 33 | 20.3 | 32.2 | | | | 561 | 9 | 564 | 9 | |
| 389 | OK | 2 | MBIO | 4/26/00 | 17:26:56 | 33 | 20.3 | 32.1 | | | | 413 | 14 | 427 | 14 | |
| 390 | OK | 2 | MBIO | 4/26/00 | 17:27:01 | 33 | 20.3 | 32.1 | | | | 343 | 19 | 360 | 19 | |
| 391 | OK | 2 | MBIO | 4/26/00 | 17:27:11 | 33 | 20.3 | 32.1 | | | | 277 | 29 | 297 | 29 | |
| 392 | OK | 2 | MBIO | 4/26/00 | 17:27:21 | 33 | 20.3 | 32 | | | | 246 | 39 | 265 | 39 | |
| 393 | OK | 2 | MBIO | 4/26/00 | 17:27:41 | 33 | 20.3 | 31.9 | | | | 211 | 59 | 234 | 59 | |
| 394 | OK | 2 | MBIO | 4/26/00 | 17:28:01 | 33 | 20.3 | 31.8 | | | | 193 | 79 | 216 | 79 | |
| 395 | OK | 2 | MBIO | 4/26/00 | 17:28:41 | 33 | 20.3 | 31.7 | | | | 181 | 119 | 194 | 119 | |
| 396 | OK | 2 | MBIO | 4/26/00 | 17:29:41 | 33 | 20.3 | 31.6 | | | | 166 | 179 | 178 | 179 | |
| 397 | OK | 2 | MBIO | 4/26/00 | 17:30:41 | 33 | 20.3 | 31.6 | | | | 155 | 239 | 168 | 239 | |
| 398 | OK | 2 | MBIO | 4/26/00 | 17:31:41 | 33 | 20.3 | 31.7 | | | | 149 | 299 | 158 | 299 | |
| 399 | OK | 2 | MBIO | 4/26/00 | 17:33:21 | 33 | 20.3 | 31.7 | | | | 145 | 399 | 151 | 399 | |
| 400 | OK | 2 | MBIO | 4/26/00 | 17:33:26 | 33 | 20.3 | 31.7 | | | | 145 | 404 | 149 | 404 | |
| 401 | OK | 4 | SWEAT | 4/26/00 | 17:33:31 | 35 | 20.5 | 31.4 | 4:04:51 | | | | | | | 0.09443 |
| 402 | OK | 4 | SWEAT | 4/26/00 | 17:33:41 | 33 | 20.5 | 31.4 | 4:05:01 | | | | | | | 0.09866 |
| 403 | OK | 1 | MION | 4/26/00 | 17:33:57 | 33 | 20.3 | 31.1 | 4:05:17 | -4.4 | 0.32 | | | | | |
| 404 | OK | 1 | MION | 4/26/00 | 17:36:36 | 33 | 20.3 | 31.6 | 4:07:56 | -5.3 | 0.32 | | | | | |
| 405 | OK | 4 | SWEAT | 4/26/00 | 17:36:41 | 35 | 20.5 | 31.9 | 4:08:01 | | | | | | | 0.06199 |
| 406 | OK | 2 | MBIO | 4/26/00 | 17:36:51 | 33 | 20.3 | 32.1 | | | | 642 | 9 | 513 | 9 | |
| 407 | OK | 2 | MBIO | 4/26/00 | 17:36:56 | 33 | 20.3 | 32.1 | | | | 475 | 14 | 385 | 14 | |
| 408 | OK | 2 | MBIO | 4/26/00 | 17:37:01 | 33 | 20.3 | 32.2 | | | | 397 | 19 | 323 | 19 | |
| 409 | OK | 2 | MBIO | 4/26/00 | 17:37:11 | 33 | 20.3 | 32.2 | | | | 326 | 29 | 263 | 29 | |
| 410 | OK | 2 | MBIO | 4/26/00 | 17:37:21 | 33 | 20.3 | 32.2 | | | | 289 | 39 | 236 | 39 | |
| 411 | OK | 2 | MBIO | 4/26/00 | 17:37:41 | 33 | 20.3 | 32.3 | | | | 253 | 59 | 208 | 59 | |
| 412 | OK | 2 | MBIO | 4/26/00 | 17:38:01 | 33 | 20.3 | 32.3 | | | | 234 | 79 | 193 | 79 | |
| 413 | OK | 2 | MBIO | 4/26/00 | 17:38:41 | 33 | 20.3 | 32.4 | | | | 211 | 119 | 180 | 119 | |
| 414 | OK | 2 | MBIO | 4/26/00 | 17:39:41 | 33 | 20.3 | 32.5 | | | | 194 | 179 | 169 | 179 | |
| 415 | OK | 2 | MBIO | 4/26/00 | 17:40:41 | 33 | 20.3 | 32.6 | | | | 182 | 239 | 162 | 239 | |
| 416 | OK | 2 | MBIO | 4/26/00 | 17:41:41 | 33 | 20.3 | 32.6 | | | | 174 | 299 | 157 | 299 | |
| 417 | OK | 2 | MBIO | 4/26/00 | 17:43:21 | 33 | 20.3 | 32.6 | | | | 165 | 399 | 151 | 399 | |
| 418 | OK | 2 | MBIO | 4/26/00 | 17:43:26 | 33 | 20.3 | 32.5 | | | | 163 | 404 | 150 | 404 | |
| 419 | OK | 4 | SWEAT | 4/26/00 | 17:43:31 | 35 | 20.5 | 32.3 | 4:14:51 | | | | | | | 0.105 |

FIG. 2

| mglog record # | record status OK or CORRUPT | Date | Time | Event Code UNCAL (START), CAL, ERR_, MEAL, SNACK, SLEEP, etc. | BG Reading | Check Sum |
|---|---|---|---|---|---|---|
| 0 | OK | 4/26/00 | 13:28 | UNCAL | 0 | 607 |
| 1 | OK | 4/26/00 | 16:43 | CAL | 65 | 05A0 |
| 2 | OK | 4/26/00 | 17:03 | ERR63 | --- | 072F |
| 3 | OK | 4/26/00 | 17:23 | ERR63 | --- | 732 |
| 4 | OK | 4/26/00 | 17:43 | ERR36 | --- | 785 |
| 5 | OK | 4/26/00 | 18:03 | ERR36 | --- | 733 |
| 6 | OK | 4/26/00 | 18:23 | GL OK | 193 | 654 |
| 7 | OK | 4/26/00 | 18:43 | GL OK | 166 | 657 |
| 8 | OK | 4/26/00 | 19:03 | GL OK | 146 | 653 |
| 9 | OK | 4/26/00 | 19:23 | GL OK | 148 | 658 |
| 10 | OK | 4/26/00 | 19:43 | GL OK | 133 | 067C |
| 11 | OK | 4/26/00 | 20:03 | GL OK | 116 | 672 |
| 12 | OK | 4/26/00 | 20:23 | GL OK | 107 | 675 |
| 13 | OK | 4/26/00 | 20:43 | GL OK | 109 | 067A |
| 14 | OK | 4/26/00 | 21:03 | GL OK | 95 | 064C |
| 15 | OK | 4/26/00 | 21:23 | GL OK | 92 | 064C |
| 16 | OK | 4/26/00 | 21:43 | GL OK | 79 | 654 |
| 17 | OK | 4/26/00 | 22:03 | GL OK | 93 | 064E |
| 18 | OK | 4/26/00 | 22:23 | GL OK | 96 | 654 |
| 19 | OK | 4/26/00 | 22:43 | GL OK | 83 | 653 |
| 20 | OK | 4/26/00 | 22:50 | MODE | 0 | 5.00E+06 |
| 21 | OK | 4/26/00 | 22:51 | LOLIM | 40 | 674 |
| 22 | OK | 4/26/00 | 23:03 | GL OK | 90 | 648 |
| 23 | OK | 4/26/00 | 23:23 | GL OK | 93 | 064E |
| 24 | OK | 4/26/00 | 23:43 | GL OK | 69 | 654 |
| 25 | OK | 4/27/00 | 0:03 | ERR63 | --- | 075D |
| 26 | OK | 4/27/00 | 0:23 | ERR63 | --- | 760 |
| 27 | OK | 4/27/00 | 0:43 | ERR63 | --- | 763 |
| 28 | OK | 4/27/00 | 1:03 | GL OK | 69 | 651 |
| 29 | OK | 4/27/00 | 1:23 | GL OK | 76 | 652 |
| 30 | OK | 4/27/00 | 1:43 | ERR63 | --- | 075E |
| 31 | OK | 4/27/00 | 2:03 | ERR36 | --- | 075C |
| 32 | OK | 4/27/00 | 2:23 | GL OK | 85 | 064D |
| 33 | OK | 4/27/00 | 2:43 | GL OK | 73 | 064D |
| 34 | OK | 4/27/00 | 3:03 | GL OK | 84 | 064D |
| 35 | OK | 4/27/00 | 3:23 | GL OK | 80 | 064C |
| 36 | OK | 4/27/00 | 3:43 | GL OK | 89 | 658 |
| 37 | OK | 4/27/00 | 4:03 | GL OK | 79 | 655 |
| 38 | OK | 4/27/00 | 4:23 | GL OK | 73 | 652 |
| 39 | OK | 4/27/00 | 4:26 | ENDSEQ | --- | 07D9 |

FIG. 3

FORMULATION AND MANIPULATION OF DATABASES OF ANALYTE AND ASSOCIATED VALUES

CROSS-REFERENCE TO RELATED APPLICATIONS

This application is a continuation of U.S. application Ser. No. 10/460,557 12, Jun. 2003, now allowed, which is a continuation of U.S. application Ser. No. 09/927,583 filed 10 Aug. 2001, now U.S. Pat. No. 6,633,772, which claims the benefit of U.S. Provisional Application Ser. No. 60/226,205, filed 18 Aug. 2000, all of which applications are herein incorporated by reference in their entireties.

TECHNICAL FIELD

The present invention relates to the formulation of analyte data points, derived data, and data attributes into one or more databases, the databases themselves, and the manipulation of those databases to produce useful information regarding factors correlated with analyte data.

BACKGROUND OF THE INVENTION

Previously, measurement of analyte levels in an individual was inconvenient and time consuming. For example, monitoring blood glucose levels in a diabetic formerly required a diabetic subject to obtain a blood sample, test that sample using e.g., a HemoCue® (Aktiebolaget Leo, Helsingborg, Sweden) clinical analyzer. Such methods typically require a finger-stick for each measurement. As a result, testing of blood glucose levels was seldom performed more frequently than 2 times per day. Such testing does not provide a complete picture of the fluctuations of glucose levels. In addition, unless the subject manually recorded the blood glucose level measured, that information was preserved only in the subject's memory. Further information regarding other factors that could affect the user's blood glucose levels, such as food intake, physical activity, etc., were similarly lost. Written records were reliable only to the extent the subject was diligent about recording information accurately and consistency. Hence, formulation of a database comprising (1) data points (e.g., measured analyte levels) and (2) information associated with each data point (e.g., the date and time of the measurement; activities affecting analyte levels such as food or water intake or physical exertion; and drug administration), was previously difficult. Further, even if obtainable, the accuracy and precision of such databases was suspect.

The present invention provides a novel method of formulating analyte data databases, analyte data databases themselves, and methods of manipulating the analyte data databases to produce useful information, e.g., for analyzing factors suspected of affecting analyte levels and investigating the efficacy of drug action for a large number of experimental subjects.

SUMMARY OF THE INVENTION

The present invention relates to methods of formulating analyte data databases (comprising, analyte data points, derived data, and data attributes), the analyte data databases themselves, and to methods for manipulating and analyzing the analyte data databases.

In one aspect the present invention relates to methods of formulating one or more analyte data databases (comprising, analyte data points, derived data, and data attributes). The databases may comprise information obtained for one or more analytes. In one embodiment of the methods, analyte measurement values are collected from one or more subject using an analyte monitoring device for each subject. The analyte monitoring device may comprise a transdermal sampling device. Typically, the analyte monitoring device is capable of providing frequent analyte measurement values, wherein the analyte measurement values comprise acquired data points that are specifically related to analyte amount or concentration in the subject. These data points may be acquired at selected time intervals. One or more analyte data databases are then formulated by associating each of the data points with one or more data attributes.

In a further embodiment, the data points comprise derived data determined from one or more acquired data points and the derived data are associated with the data points from which they are derived. Further, the derived data may be associated with one or more data attributes.

Analyte measurement values used in these methods may be collected from a single individual or from more than one individual. An analyte monitoring device is used by each individual during the course of obtaining the analyte measurement values. The analyte measurement values (as well as data points, derived data, and data attributes) may be compiled into one or more analyte data databases. When multiple databases are formulated, the data points collected from a single individual are typically associated with one or more relevant data attributes. The data from each individual is then compiled into a large, communal database (e.g., a data warehouse). Further, relationships may be established between the data points, derived data, and data attributes from different individuals. In addition, population databases may be formulated that comprise compilations of derived data from more than one individual (e.g., mean analyte measurement values across a selected population) as well as associated data attributes. Such population databases may be used for comparisons between different populations (e.g., males/females, different races, different age groupings, etc.).

In one embodiment of the present invention the analyte is a biological analyte, e.g., glucose. The data points may, for example, be signal measurements related to the amount or concentration of the analyte. In this case, analyte amount or concentration may itself be a derived data point. The analyte monitoring device may be capable of detecting one or more analyte. Alternatively, more than one monitoring device may be used to generate data for use in formulating the analyte data databases of the present invention. In one aspect, the analyte is at least glucose and the analyte monitoring device comprises a glucose monitoring device. A number of glucose monitoring devices may be used in the practice of the present invention. In a preferred embodiment, the glucose monitoring device comprises a transdermal sampling device, a sensing device, a display, and means to provide an audible alert when glucose levels in a subject being monitored are outside of a predetermined range. The sensing device may, for example, comprise electrochemical devices, optical, chemical devices, and combinations thereof. In one aspect the sensing device comprises an electrochemical sensor and the acquired data points comprise electrochemical signals.

Data attributes include, but are not limited to, the following: chronological information, user perspiration levels, device operating temperature, missed measurements; skipped measurements, user body temperature, user skin conductance, environmental variables, alarm events, activity codes, total excursion, mean value, statistical function, subject code, demographic information, physical characteristics, and disease-associated characteristics.

The present invention also comprises an analyte data database formulated by the above method. For example, an analyte data database may be formulated from data points collected using an analyte monitoring device, the analyte monitoring device (i) comprising a transdermal sampling device, and (ii) providing frequent analyte measurement values. The analyte measurement values may comprise data points that are specifically related to analyte amount or concentration. In the database, the data points are associated with one or more relevant data attributes.

The present invention also includes methods for manipulating one or more analyte data database. Such methods of manipulating the databases of the present invention are described in greater detail herein below. For example, one such method comprises one or more analyte data database of the present invention and manipulating the data points via the attributes associated with the data points to determine relationships between the data points and the attributes. Alternatively, or in addition to the previous method, using one or more analyte data databases of the present invention, the attributes may be manipulated via the data points associated with the attributes to determine relationships between the attributes and the data points.

These and other embodiments of the present invention will readily occur to those of ordinary skill in the art in view of the disclosure herein.

BRIEF DESCRIPTION OF THE FIGURES

FIGS. 1A, 1B, 2, and 3 provide examples of tabular databases of the present invention. FIG. 1B is a continuation of FIG. 1A. The data appearing in FIGS. 1A/1B and 2 was collected from a single individual over the course of a single data collection run using a GlucoWatch biographer. FIG. 1A/1B is a tabulation of unanalyzed data collected during the first one hour, five minutes of the data collection run, and prior to calibration of the biographer device. FIG. 2 is a tabulation of unanalyzed data obtained over a 20-minute period during the same run, but after calibration of the biographer device. FIG. 3 is a tabulation of analyzed data derived from the data points collected during this run. In particular, the highlighted information in row 4 of FIG. 3 was derived from the data points appearing in FIG. 2.

DETAILED DESCRIPTION OF THE INVENTION

Figure 4:
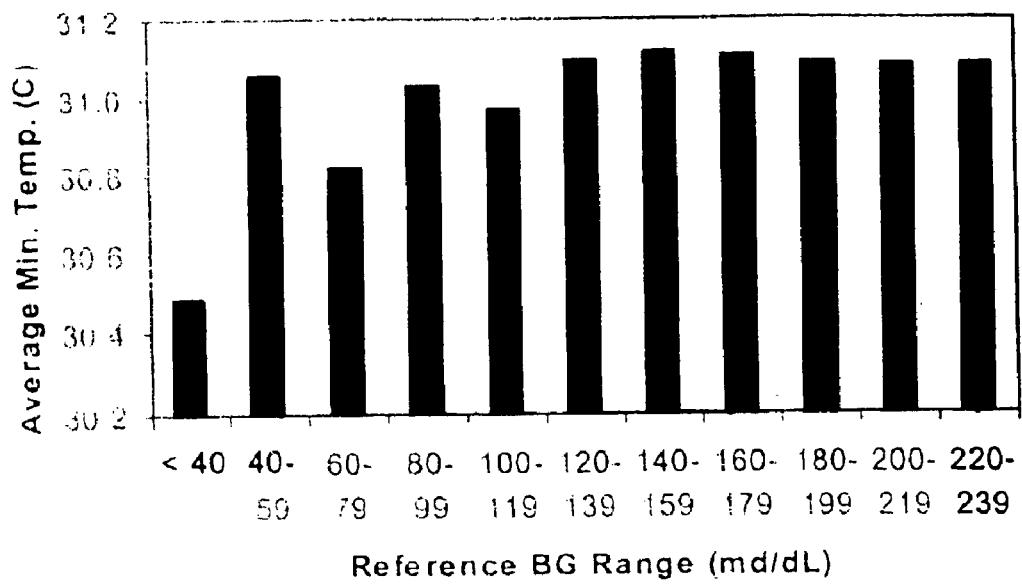
FIG. 4 presents data concerning average minimum temperature during each biographer measurement cycle vs. reference blood glucose.

The practice of the present invention employs, unless otherwise indicated, conventional methods of database storage and manipulation, within the skill-of the art. Such techniques are explained fully in the literature. See, e.g., Numerical Mathematical Analysis, Third Edition, by J. B. Scarborough, 1955, John Hopkins Press, publisher; System Analysis and Design Methods, by Jeffrey L. Whitten, et al., Fourth Edition, 1997, Richard D. Irwin, publisher; Modern Database Management, by Fred R. McFadden, et al., Fifth Edition, 1999, Addison-Wesley Pub. Co., publisher; Modern System Analysis and Design, by Jeffery A. Hoffer, et al., Second Edition, 1998, Addison-Wesley Pub. Co., publisher; Data Processing: Fundamentals, Design, and Implementation, by David M. Kroenke, Seventh Edition, 2000, Prentice Hall, publisher; Case Method: Entity Relationship Modelling (Computer Aided Systems Engineering), by Richard Barker, 1990, Addison-Wesley Pub Co., publisher.

All publications, patents and patent applications cited herein, whether supra or infra, are hereby incorporated by reference in their entirety.

1. DEFINITIONS

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting. Abused in this specification and the appended claims, the singular forms "a", "an" and "the" include plural referents unless the content clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology is used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device, "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5 Sep. 1991; U.S. Pat. No. 5,636,632), suction, electroporation, thermal poration, passive diffusion (see, e.g., International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; International Publication WO 99/44507, published 1999 Sep. 10; International Publication WO 99/44638, published 1999 Sep. 10; and International Publication WO 99/40848, published 1999 Aug. 19). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" or "analyte monitoring device" refer to a system useful for obtaining frequent measurements of a physiological analyte present in a biological system. Such a device is useful, for example, for monitoring the amount or concentration of an analyte in a subject. Such a system may comprise, but is not limited to, a sampling mechanism, a sensing mechanism, and a microprocessor mechanism in operative communication with the sampling mechanism and the sensing mechanism. Such a device typically provides frequent measurement or determination of analyte amount or concentration in the subject and provides an alert or alerts when levels of the analyte being monitored fall outside of a predetermined range. Such devices may comprise durable and consumable (or disposable) elements. The term "glucose monitoring device" refers to a device for monitoring the amount or concentration of glucose in a subject. Such a device typically provides a frequent measurement or determination of glucose amount or concentration in the subject and provides an alert or alerts when glucose levels fall outside of a predetermined range. One such exemplary glucose monitoring device is the GlucoWatch biographer available from Cygnus, Inc., Redwood City, Calif., US. The GlucoWatch biographer comprises two primary elements, a durable element (comprising a watch-type housing, circuitry, display element, microprocessor element, electrical connector elements, and may further comprise a power supply) and a consumable, or disposable, element (e.g., an AutoSensor component involved in sampling and signal detection, see, for example, WO 99/58190, published 18 Nov. 1999). This and similar devices is described, for example, in the following publications: Tamada, et al., (1999) *JAMA* 282:1839–1844; U.S. Pat. No. 5,771,890, issued 30 Jun. 1998; U.S. Pat. No. 5,735,273, issued 7 Apr. 1998; U.S. Pat. No. 5,827,183, issued 27 Oct. 1998; U.S. Pat. No. 5,954,685, issued 21 Sep. 1999; U.S. Pat. No. 5,989,409, issued 23 Nov. 1999; U.S. Pat. No. 6,023,629, issued 8 Feb. 2000; EP Patent Application EP 0 942 278 A2, published 15 Sep. 1999; PCT International Application WO 96/001100, published 4 Jan. 1996; PCT International Application WO 99/58190, published 18 Nov. 1999. The GlucoWatch biographer provides a device for frequent sampling of glucose from a subject the application of low intensity electric fields across the skin (iontophoresis) to enhance the transport of glucose from body tissues to a sampling chamber. In addition, when the concentration or amount of glucose has been determined to be outside of a predetermined range of values the GlucoWatch biographer produces an alert or alarm signal. Such an alert or alarm is a component of the GlucoWatch biographer.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g, second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal-tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch® (Cygnus, Inc., Redwood City, Calif.) biographer glucose monitor (See, e.g., Tamada et al. (1999) JAMA 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," or "sensing mechanism," encompasses any device that can be used to measure the concentration or amount of an analyte, or derivative thereof, of interest. Preferred sensing devices for detecting blood analytes generally include electrochemical devices, optical and chemical devices and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U. S. Pat. No. 5,747,806).

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al.(1995) Analytical Chemistry 67:4594–4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997. The ionically conductive material may comprise a biocide. For example, during manufacture of an AutoSensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a mask layer, collection insert layer, a gel retaining layer, an electrode assembly, and a support tray. The AutoSensor assembly may also include liners where the layers are held in approximate, functional relationship to each other. Exemplary collection assemblies and AutoSensor structures are described, for example, in International Publication WO 99/58190, published 18 Nov. 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses both positive and negative effects on the physiology of a subject. One example of a positive physiological effect, is a treatment of a subject that achieves the purpose of the therapy. Typically, a positive physiological effect means that the symptoms of the subject being treated are prevented or alleviated. For example, a positive physiological effect would be the prolongation of survival in a patient being treated for one or more condition or disorder An example of negative physiological effects is the effect of severe hypoglycemia in a human subject, such negative physiological effects may include confusion, blurring of vision, seizure, and ultimately loss of consciousness or seizure.

"Parameter" refers to an arbitrary constant or variable so appearing in a mathematical expression that changing it gives various cases of the phenomenon represented (McGraw-Hill Dictionary of Scientific and Technical Terms, S. P. Parker, ed., Fifth Edition, McGraw-Hill Inc., 1994). A parameter is any of a set of properties whose values determine the characteristics or behavior of something.

"Decay" refers to a gradual reduction in the magnitude of a quantity, for example, a current detected using a sensor electrode where the current is correlated to the concentration of a particular analyte and where the detected current gradually reduces but the concentration of the analyte does not.

"Skip" or "skipped" signals refer to data that do not conform to predetermined criteria (for example, error-associated criteria as described in U.S. Pat. No. 6,233,471, herein incorporated by reference). A skipped reading, signal, or measurement value typically has been rejected (i.e., a "skip error" generated) as not being reliable or valid because it does not conform with data integrity checks, for example, where a signal is subjected to a data screen which invalidates incorrect signals based on a detected parameter indicative of a poor or incorrect signal.

A "data point", generally, is a numeric value which corresponds to a physical measurement (an "acquired" datum or data point) or to a single numeric result calculated or derived from one or more acquired data points (a "calculated" or "derived" datum or data point). Derived data include, but are not limited to, derived quantities from original data, such as, rate and/or magnitude of change, slope of a line (e.g., as determined by regression analysis), an intercept (e.g., as determined by regression analysis), and correlation coefficients.

"Data tags," also referred to as "attributes" of a data point, are various characteristics of the particular data point with which they are associated. For example, data points comprising glucose concentrations or amounts measured with the GlucoWatch biographer are associated with a number of attributes, e.g., the date and time the measurement was taken; certain identification related to the particular user from which the measurement was made (e.g., demographic information such as the particular user's sex, age, weight; medical information e.g., the type of disease suffered by the user).

A "database" is a collection of data points and data attributes associated with each data point. Thus, an "analyte data points, derived data, and data attributes database" is a database comprising data points collected, e.g. by an analyte monitoring device, data derived from the original data points and the data attributes associated with those data points or the derived data. A database may be limited to data points comprising measurements of one or more analyte levels; those data points may further be collected from one or more subjects. For example, one analyte data point database may be created and the information in the database related to a second database of attributes. Such combinations of one or more databases are within the skill of one of ordinary skill in the art in view of the teachings of the present specification. A "data warehouse" is another term for database. The term data warehouse is typically applied to large databases.

"Formulation" of a database comprises collecting data points, inputing those data points into a desired database format, and associating various attributes with each data point according to the particular format employed. A wide variety of software exists which provides a means for inputing data points, and associating the data points with data attributes, such as Excel® (Microsoft® Corporation, Seattle, Wash.) spreadsheet software, Quattro® (Corel Inc., Ottawa, Canada) spreadsheet software, Microsoft Access 2000® (Microsoft) software, Oracle® (Oracle Inc., Redwood Shores, Calif.) software, as well as other database and data warehousing software.

"Manipulation" of a database refers to a variety of processes, e.g., selecting, sorting, sifting, aggregating, clustering, modeling, exploring, and segmenting data points using various data attributes or tags associated with the data points. Available systems for generating databases and manipulating the resulting databases include but are not limited to Sybase® (Sybase Systems, Emeryville, Calif.), Oracle® (Oracle Inc., Redwood Shores, Calif.), and Sagent Design Studio® (Sagent Technologies Inc., Mountain View, Calif.) systems software. Further, statistical packages and systems for data analysis and data mining are also available. Illustrative examples include SAS® (SAS Institute Inc., Cary, N.C.) and SPSS® (SPSS Inc., Chicago, Ill.) systems software.

"Data mining" refers to the process of selecting, exploiting, modeling, etc., large amounts of data to uncover previously unknown trends, patterns, and relationships within and among various data points and data attributes.

"Data aggregation" and "data clustering" refers to the process of grouping data points on the basis of one or more common attributes. Conversely, "data segmentation" refers to the process of differentiating data into discrete groups on the basis of one or more attributes.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1 GENERAL OVERVIEW OF THE INVENTION

The present invention relates to a method for formulating an analyte data points, derived data, and data attributes database (referred to herein as analyte data databases), comprising data points corresponding to measured values of one or more analytes collected by an analyte measurement device, and one or more relevant attributes associated with each data point. The present invention also relates to analyte data databases.

Further, the invention relates to the manipulation of a database of the present invention by means of data attributes in order to examine factors which affect baseline analyte levels and/or changes thereto: for example, analysis of data related to physiological effects, such as the rate of change of an analyte in a subject. The analyte data databases may also be manipulated through the data points, derived data, and/or data attributes, as well as combinations thereof.

Recent advances in analyte monitoring device technology now permit periodic measurement of analyte levels for a large number of users with a consistency and frequency that was not previously possible. For example, the GlucoWatch biographer automatically measures a user's blood glucose levels approximately three times every hour. Thus, analyte monitoring devices such as the GlucoWatch biographer make it possible to generate sufficient data regarding analyte levels to permit the formulation of analyte data points, derived data, and data attributes databases of unprecedented size and scope.

Tagging the data points after collection permits manipulation of the database to produce useful information, e.g., information regarding factors that affect or are correlated with baseline analyte levels and/or changes therein.

2.2 DATABASE FORMULATION

The method of formulating an analyte data points, derived data, and data attributes database (i.e., analyte data databases) according to the present invention may comprise the following: (1) the periodic collection of data points, said data points comprising measurements made by an analyte monitoring device, for example, a current measurement that is ultimately correlated with an analyte amount or concentration; and (2) the association of those data points with relevant data point attributes. The method may further comprise (3) determining derived data points from one or more direct data points and (4) associating those data points with relevant data point attributes.

In one version of the present invention, the data points are collected from a single individual. In an alternate embodiment, data points are collected from multiple individuals and compiled into an aggregate or population database, either at the time the points are collected or subsequently.

The analyte monitoring device used to collect data points may be capable of measuring a single analyte. Alternately, the device may be capable of measuring multiple analytes, and data points for each are collected and compiled into a multi-analyte data database. In still another embodiment, the database is formulated by compiling data points collected using several analyte monitors, each of which measures a single analyte, resulting in a multi-analyte data database. Examples of analytes, both biological and non-biological, are detailed in the subsection herein entitled "Exemplary Analytes."

In the case of multi-analyte data databases, wherein the analytes are biological analytes, all of the analytes may be related to a single physiologic state or condition; alternately, each analyte may be relevant to a different physiological state or condition. Details of exemplary data points, exemplary data attributes, and exemplary methods for associating data points with relevant data attributes are described in detail in the following subsections.

An exemplary analyte monitoring device is a glucose monitoring system which provides frequent measurements of glucose amount or concentrations, e.g., the GlucoWatch biographer system. This system is a wearable, non-invasive glucose monitoring system that provides a glucose reading automatically every twenty minutes. The GlucoWatch biographer system has several advantages including, but not limited to, the fact that its non-invasive and non-obtrusive nature encourages more frequent glucose testing among people (or animals) with diabetes. Of greater clinical relevance is the frequent nature of the information provided. Prior to the GlucoWatch biographer system no method existed for frequent glucose measurement outside of invasive means, often requiring hospital care (Mastrototaro, J. J., and Gross, T. M., "Clinical Results from the MiniMed Continuous Glucose Monitoring System" Proc. 31$^{st}$ Annual Oak Ridge Conference, April, 1999). The GlucoWatch biographer system provides more frequent monitoring often desired by physicians in an automatic, non-invasive, and user-friendly manner. The automatic nature of the system also allows monitoring to continue even while a user is sleeping or otherwise unable to test.

The GlucoWatch biographer system comprises: (a) iontophoretic transport of glucose across the skin to non-invasively sample the glucose in the subject, (b) an electrochemical biosensor to measure the glucose concentration in the extracted sample, and (c) an intelligent data-processing algorithm that coverts the raw biosensor signals to glucose readings while safeguarding against erroneous results through data point screening routines. These three aspects of the system are briefly described below and are described more extensively in the publications referenced in the "Definitions" section, above.

The first aspect of the system is the iontophoretic extraction of glucose. Many small molecules are transported through the skin by either passive or facilitated means. Passive transport of compounds such as nicotine, estradiol, testosterone, etc. is the basis of transdermal drug delivery (skin patches). Transport through human skin can be greatly enhanced by the application of an electric field gradient. The use of a low-level electric current to enhance transport is known, generically, as iontophoresis.

Iontophoretic transport through skin can occur in either direction (Glikfeld, P., et al., Pharm. Res. 6, 988–990 (1989)). In particular, it was shown that small molecules such as glucose, ethanol, and theophylline are readily transported through the skin into an external collection chamber. Because transport through the skin is in the opposite direction to that used in iontophoretic drug delivery, this effect was described as "reverse iontophoresis" (U.S. Pat. No. 5,362,307, issued Nov. 8, 1994.; U.S. Pat. No. 5,279,543, issued Jan. 18, 1994.; U.S. Pat. No. 5,730,714, issued Mar. 24, 1998). In fact, because glucose is an uncharged molecule, transport is achieved through electro-osmosis. Results obtained from analyses using the GlucoWatch biographer system showed that extracted glucose correlated closely with blood glucose (Tamada, J. A., et al., JAMA 282:1839–1844, 1999).

Figure 9:
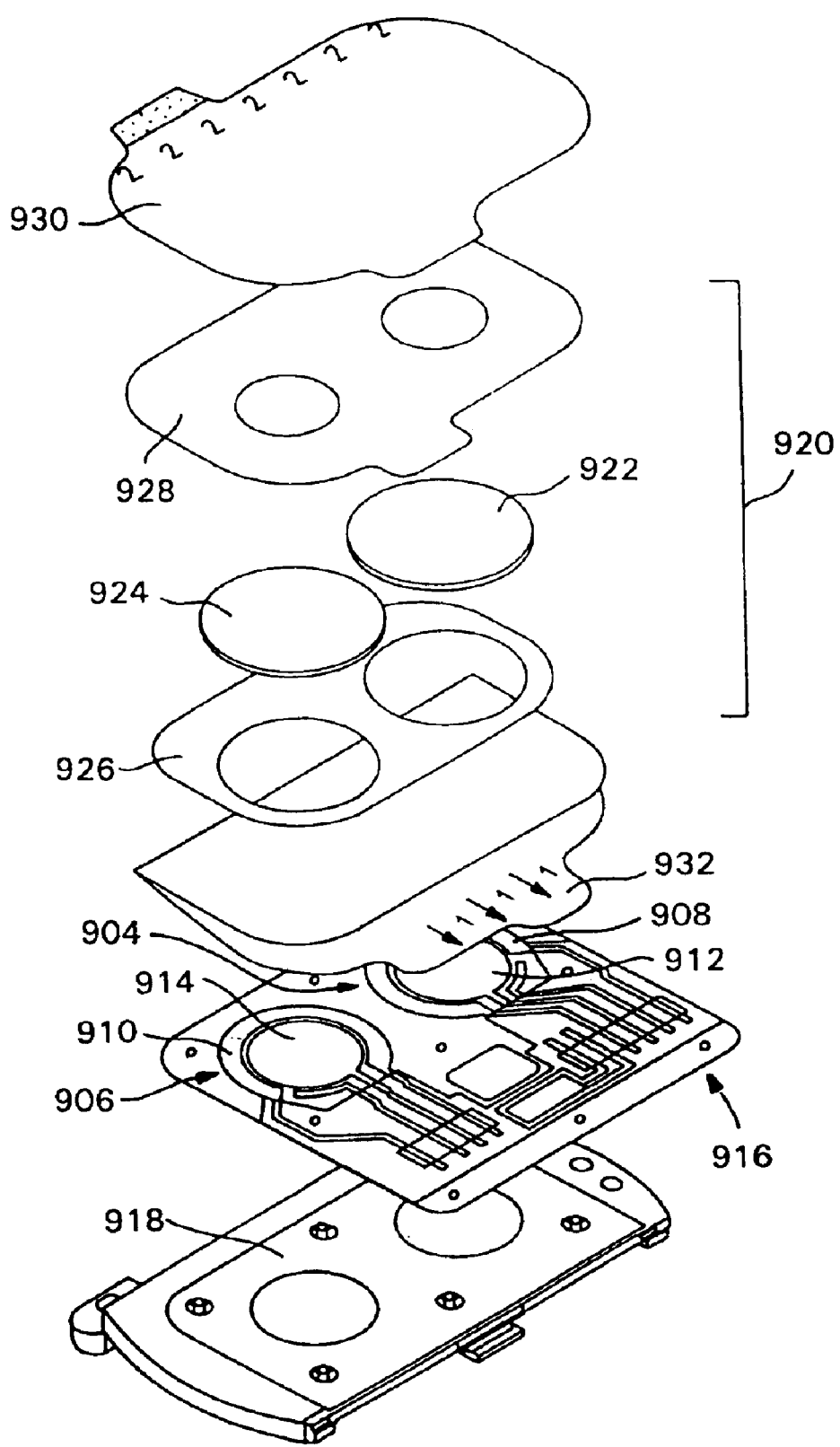
FIG. 9 presents a schematic of an exploded view of exemplary components comprising one embodiment of an AutoSensor for use in a monitoring system.

The second aspect of the system involves the use of an electrochemical glucose biosensor. The GlucoWatch biographer system utilizes an electrochemical biosensor assembly to quantitate the glucose extracted through the skin. There are two biosensors in the GlucoWatch biographer system (FIG. 9). Each biosensor consists of a hydrogel pad containing the enzyme glucose oxidase (GOx) and a set of electrodes. One surface of the hydrogel pad contacts the skin while the opposite surface is in contact with the biosensor and iontophoresis electrodes. The hydrogel pads serve two functions as follows. During iontophoresis the pads serve as the electrical contacts with the skin and the collection reservoirs for the extracted glucose. During the sensing portion of the cycle, the glucose extracted through the skin reacts with the GOx in the hydrogel pads via the reaction:

$$\text{Glucose} + O_2 \xrightarrow{\text{GOx}} \text{Gluconic acid} + H_2O_2.$$

The $H_2O_2$ produced by this reaction is then detected amperometrically at the platinum/carbon working electrode of the sensor. The integrated sensor current measured is proportional to the concentration of $H_2O_2$, and ultimately to the amount of glucose extracted. The extraction and sensing portions of the cycle occur in succession, and the cycle repeats to provide a measurement of glucose every twenty minutes.

For convenience to the user, the GlucoWatch biographer system was developed as a miniaturized device which can be worn on the wrist, forearm, upper arm, or other body part. The GlucoWatch biographer system durable component contains electronics for the biosensors and iontophoresis, a microprocessor, data storage memory, and an LCD display. Two sets of biosensors and iontophoresis electrodes are fitted onto the skin side of the device (e.g., a consumable component, the AutoSensor). A schematic diagram of the AutoSensor of the GlucoWatch biographer system is shown in FIG. 9.

Referring to FIG. 9, an exploded view of exemplary components comprising one embodiment of an AutoSensor for use in an iontophoretic sampling system is presented. The AutoSensor components include two biosensor/iontophoretic electrode assemblies, 904 and 906, each of which have an annular iontophoretic electrode, respectively indicated at 908 and 910, which encircles a biosensor electrode 912 and 914. The electrode assemblies 904 and 906 are printed onto a polymeric substrate 916 which is maintained within a sensor tray 918. A collection reservoir assembly 920 is arranged over the electrode assemblies, wherein the collection reservoir assembly comprises two hydrogel inserts 922 and 924 retained by a gel retaining layer 926 and mask layer 928. Further release liners may be included in the assembly, for example, a patient liner 930, and a plow-fold liner 932. In one embodiment, the electrode assemblies comprise bimodal electrodes. A mask layer 928 (for example, as described in PCT Publication No. WO 97/10356, published 20 Mar. 1997, and U.S. Pat. Nos. 5,735,273, 5,827,183, 6,141,573, and 6,201,979, all herein incorporated by reference) may be present. Other AutoSensor embodiments are described in WO 99/58190, published 18 Nov. 1999, herein incorporated by reference.

The mask and retaining layers are preferably composed of materials that are substantially impermeable to the analyte (e.g., glucose) to be detected (see, for example, U.S. Pat. Nos. 5,735,273, and 5,827,183, both herein incorporated by reference). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 9 are for use in a automatic sampling system which is configured to be worn like an ordinary wristwatch, as described, for example, in PCT Publication No. WO 96/00110, published 4 Jan. 1996, herein incorporated by reference. The wristwatch housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The third aspect of the system is an intelligent data-processing algorithm that coverts the raw biosensor signals to glucose readings while safeguarding against erroneous results through data point screening routines. The raw current data obtained from the biosensors must be converted into an equivalent blood glucose value. Equations to perform this data conversion have been developed, optimized, and validated on a large data set consisting of GlucoWatch and reference blood glucose readings from clinical trials on diabetic subjects (see, for example, WO 018289A1, published 6 Apr. 2000). This data conversion algorithm is programmed into a dedicated microprocessor in the GlucoWatch biographer system. The software also contains screens to exclude spurious data points that do not conform to objective, a priori criteria (e.g., data which contain noise above a certain threshold). Exemplary signal processing applications include, but are not limited to, those taught in U.S. Pat. Nos. 6,144,869, 6,233,471, 6,180,416, herein incorporated by reference.

In addition to the two glucose biosensors, the GlucoWatch biographer system also contains a temperature sensor and a skin conductivity sensor. Input from the former is used to exclude data points obtained during large thermal excursions. The skin conductivity input is used to exclude data obtained when the subject is perspiring profusely, as sweat contains glucose which may confound the value obtained for the extracted sample. Hence, these various screens reject data points that may provide false glucose information. The remaining data points are then suitable for clinical use.

The GlucoWatch biographer system is housed in a plastic case held in place, typically on the arm, with a wrist band. A single AAA battery is used as the primary power source with an additional back-up battery. The GlucoWatch circuitry includes a microprocessor and a custom application specific integrated circuit (ASIC) chip containing the circuitry to run both the iontophoresis and biosensor functions. There is sufficient memory to store up to 4000 glucose readings which represents approximately three months of data with daily use. An LCD display and four push buttons on the face of the GlucoWatch biographer system comprise the user interface, and allow the user to control and customize the functions of the monitor as well as to display clock time and date, glucose readings, and GlucoWatch operation status. Data can also be downloaded to, for example, a PC via a serial interface-adapter.

Included in the software control is the ability for the user to select high and low glucose alert levels. If the GlucoWatch biographer system measures a glucose value outside of these alert levels, an alarm sounds to notify the user of the situation.

The disposable portion of the GlucoWatch biographer system is the AutoSensor, which contains the two sets of biosensor and iontophoresis electrodes and the corresponding hydrogel discs housed held in a pre-aligned arrangement by a mask layer. The AutoSensor snaps into the skin-side of the GlucoWatch biographer system to make the necessary electrical connections between the two portions.

The GlucoWatch biographer system also contains a thermistor to measure skin temperature, and a set of conductivity probes which rest on the surface of the skin to measure skin conductivity, a measure of perspiration. As described above, the temperature and sweat data are used in the present device to ensure that the biosensor data has not been affected by large temperature excursions or perspiration during the reading period.

In another embodiment of a monitoring system, the sampling/sensing mechanism and user interface may be found on separate components (e.g., WO 00/47109, published 17 Aug. 2000). Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

2.3 EXEMPLARY ANALYTES

The analyte can be any specific substance, component, or combinations thereof that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse (e.g., ethanol, cocaine), therapeutic and/or pharmacological agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), environmental analytes (e.g., pesticides) and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent. Further, multiple analytes may be evaluated using a single sampling mechanism and the same, or different, sensing means.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used, as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

Preferably, the biosensor electrode is able to detect the analyte that has been extracted into the one or more collection reservoirs when present at nominal concentration levels. Suitable biosensor electrodes and associated sampling systems as described in are described in PCT Publication Nos. WO 97/10499, published 20 Mar. 1997 and WO 98/42252, published 1 Oct. 1998.

2.4 DATA POINTS

Figure 1B:
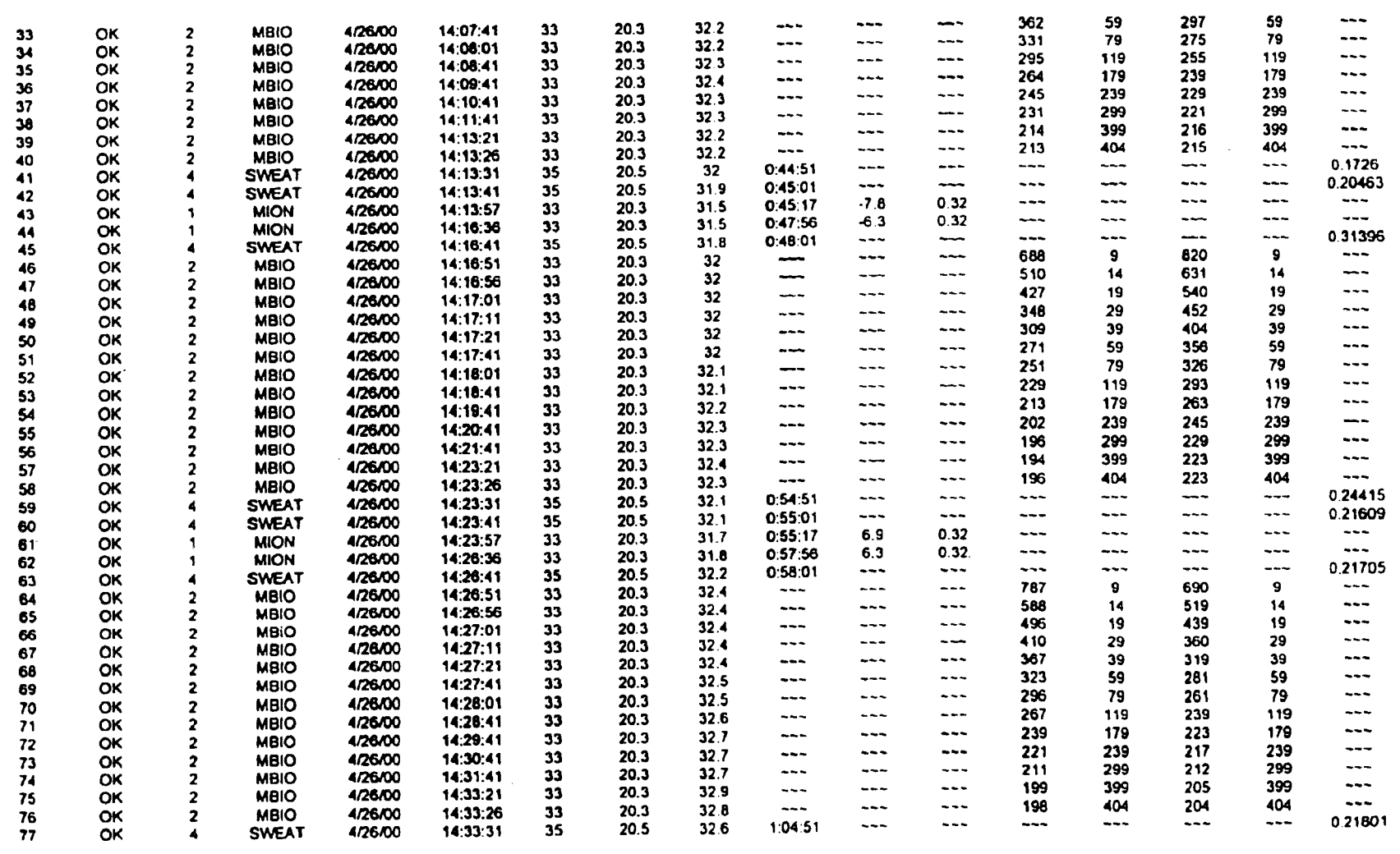

The method of formulating an analyte data points, derived data, and data attributes database that is the subject of the present invention begins with the collection of data sets of analyte measurement values. Typically, those sets comprise different values collected at frequent, periodic intervals over a relatively long time span. In a preferred embodiment of the invention, those data points are collected using an automatic analyte monitoring device, e.g. the GlucoWatch biographer described above For example, FIGS. 1 and 2 are tabulations of unanalyzed data collected using a GlucoWatch biographer from a single individual during a single data collection run. FIG. 1A/1B represents data points collected prior to calibrating the biographer device, while FIG. 2 represents data points collected after calibrating the device. Calibration was carried out using a single blood glucose value obtained using a finger stick glucometer, e.g., the HemoCue clinical analyzer.

The data attributes represented by each of the columns in FIGS. 1 and 2 are as follows. Column 1 provides a reference record number denominated MGLOG RECORD #. Column 2 provides information regarding the status of the record, i.e., whether the record is OK or CORRUPT, the latter indicating e.g., the occurrence of a memory error or problem caused by a write-to-memory error or a microprocessor problem. Column 3 provides information regarding the LOG ENTRY TYPE, a number that refers to the type of record found in that row. 1=MION, i.e., an iontophoretic record; 2=MBIO, i.e., a biosensor record; 3=START, NEWBAT, etc., i.e., external events; and 4=SWEAT, i.e., a sweat record. Column 4 lists the RECORD TYPE i.e., the acronym for the record type corresponding to the number present in the LOG ENTRY TYPE column.

Note that each row contains data for only one record type, the type being indicated numerically in the LOG ENTRY TYPE column and via an alphabetic acronym in the RECORD TYPE column. Hence, rows that contain MION records, i.e., data related to the generation of iontophoretic current used to effect transdermal glucose, will not have entries in columns 13 through 17. Similarly, rows that contain SWEAT records (i.e., data related to readings made by the device's sweat probe) will not have entries in columns 11 through 16. Likewise, rows containing MBIO records (i.e., data related to the detection of the amount or concentration of glucose extracted transdermally) will not have entries in columns 11, 12 or 17.

Column 5 provides the date on which the measurement was performed. Column 6 provides the time of day at which the measurement was performed. Column 7 provides a SEQUENCE NUMBER, i.e., the data collection sequence being run for the collected row. Column 8 is an information slot not used in compilation of the figures. Column 9 provides TEMPERATURE information in the range of 17–32.4° C. based on a temperature reading taken by a thermocouple internal to the device. Column 10 provides the ELAPSED TIME, a data point relating the elapsed time since the watch has been placed in contact with a subject. Note that the ELAPSED TIME column does not contain data points in those rows which contain MBIO (biosensor) records, i.e., records related to the functioning of the biographer device; instead, in those rows, data regarding elapsed time is instead recorded in rows 14 and 16. Column 11 provides information concerning the iontophoretic voltage used for transdermal extraction, IONTO VOLTAGE. Column 12 provides information concerning the iontophoretic current used for transdermal extraction, IONTO CURRENT. Column 13 provides data regarding the current generated at a first sensor, wherein the current is generated based on the amount or concentration of glucose as detected using an electrochemical system, see, e.g., as described in U.S. Pat. No. 5,989,409, issued 23 Nov. 1999, SENSOR A CURRENT. Column 14 provides data regarding the amount of time that the biosensor of sensor A was used to evaluate the glucose-related current, SENSOR A ELAPSED BIOSENSOR TIME. Column 15 provides data regarding the current generated at a second sensor, wherein the current is generated based on the amount or concentration of glucose as detected using an electrochemical system, see, e.g., as described in U.S. Pat. No. 5,989,409, issued 23 Nov. 1999, SENSOR B CURRENT. Column 16 provides data regarding the amount of time that the biosensor of sensor B was used to evaluate the glucose-related current, SENSOR B ELAPSED BIOSENSOR TIME. Finally, column 17 provides data regarding a SWEAT READING using a sweat probe.

Both FIGS. 1 and 2 present extensive data sets comprising current measurements made at independent sensors which are ultimately used to determine blood glucose concentration along with other selected parameters (e.g., using, for example, a Mixtures of Experts algorithm as described in WO018289A1, published Apr. 6, 2000).

For example, FIG. 3 depicts a database comprising blood glucose level values ("BG Reading") derived from acquired data collected from a single individual using the GlucoWatch biographer, as well as a variety of attributes (or records) associated with each of those data points. The data appearing in highlighted row "4" (FIG. 3) was derived from the data presented in FIG. 2.

In FIG. 3, the attributes associated with each column are as follows. Column 1 provides a reference record number, denominated the MGLOG RECORD #. Column 2 provides information regarding the status of the record, i.e., whether the record is OK or CORRUPT, indicating the occurrence of a memory error or problem caused by e.g., a write-to-memory error or a microprocessor problem. Column 3 provides the date that the measurement was performed, and column 4 provides the time of day at which the measurement was performed.

Column 5 provides associated event codes (which in the case of the biographer are predefined in the case of user inputs), as follows. (1) UNCAL indicates that the biographer device is uncalibrated, and is primarily used to indicate in the MGLOG the start of a monitoring run. (2) START indicates the start time and date in the MLOG and MGLOG. (3) CAL indicates that the user performed a device calibration. (4) ERR indicates that a skip or a shutoff error in a given cycle of the MGLOG has occurred. (5) MEAL indicates that the user has consumed a meal; likewise, (6) SNACK indicates that the user has consumed a snack. (7) SLEEP indicates that the user is going to sleep. (8) INSULIN indicates a point at which the user administered insulin. (9) GL OK, indicates that glucose levels are within a predetermined range; (10) LOLIM, indicates that glucose levels have fallen below a predetermined minimum, i.e., a hypoglycemic event. Finally, (11) ENDSEQ indicates the final reading in a sequence of readings.

Column 6 provides a blood glucose reading when such a reading can be reported, i.e., no error has interfered with calculation. Column 7 provides a CHECK SUM, i.e., an ASCII representation of all the characters in a record row of the MGLOG; this serves to ensure data integrity.

The database formulation method of the present invention may further comprise the calculation of derived or calculated data points from one or more acquired data points. A variety of derived data points may be useful in providing information about individuals or groups during subsequent database manipulation, and are therefore typically included during database formulation. Derived data points include, but are not limited to the following: (1) maximum analyte level or concentration, determined for a selected time period (day/week/etc.); (2) minimum analyte amount or concentration, determined for a selected time period (day/week/etc.); (3) total excursion of analyte values for a selected time period, defined as the difference between the maximum and minimum analyte values for that time period; (4) mean analyte measurement value for a selected time period; (5) distribution of analyte values around the mean (i.e., standard deviation) for a selected time period; (6) the number of analyte measurements that are abnormally high or low, determined by comparing a given measurement data point with a selected value; (7) the number of measurements not determined, due to measurement device malfunction, over a selected time period; (8) the number of alarm events for a selected time period; (9) patient-specific alert status; and (10) rates or magnitude of change for any selected data point or derived data point for a selected period of time. Other derived data points will be apparent to persons of ordinary skill in the art in light of the teachings of the present specification. The amount of available data and data derived from (or arrived at through analysis of) the original data provide provides an unprecedented amount of information that is very relevant to management of diabetic diseases. For example, by examining factors associated with the number of measurements not determined, factors can be identified to help reduce this number. As another example, examining factors associated with periods of time identified with rapid rates of change of glucose values can lead to the identification of causal factors (e.g., by comparing a record of caloric intake/output times and types with a record of rapid changes in glucose values over a selected time period, an association with insufficient or badly distributed caloric daily carbohydrate intake may be identified as the cause or periods of strenuous exercise may be identified as the cause, thus allow a subject to modify behavior to better manage disease).

2.5 DATA ATTRIBUTES

Analyte measurements and derived data points are collected and calculated, respectively, and may be associated with one or more data attributes to form a database.

Data attributes are typically of several general types. The first category comprises attributes automatically input by the analyte measurement device. These include but are not limited to the following, several of which may be identified in, for example, FIGS. 2 and 3: chronological information (e.g., DATE and TIME); user perspiration levels (SWEAT READING); and device operating temperature (TEMPERATURE). Other such attributes may include, but are not limited to, the following: missed measurements; "skipped" measurements; user body temperature; user skin conductance; environmental variables (e.g., temperature, temperature changes, humidity, sun exposure, etc.) and number and type (e.g., hyperglycemic or hypoglycemic) of alarm events.

The second category comprises user inputs, including but not limited to the following: activity codes associated with various activities affecting analyte levels, such as caloric intake and/or output (e.g., food, physical activity, etc.), sleep and administration of medications, including the dose and time thereof (e.g., FIG. 1A/1B, EVENT CODE).

The third comprises data identifiers, i.e., attributes defined in terms of analyte values (maximum/minimum; hypoglycemic- or hyperglycemic-events; etc.) and/or may further include information regarding how these values were obtained, for example, total excursion, mean value, or a statistical distribution or function.

The final category comprises subject identifiers, i.e. characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., number of pregnancies, disease states or conditions, etc.); and (5) disease-associated characteristics such as the type of analyte disorder, if any; the type of medication used by the subject, if any; and the presence or absence of surrogate analyte markers (e.g., in the case of diabetes, HbAIc, a hemoglobin surrogate marker for high blood glucose). For example, the data presented in FIGS. 1, 2 and 3 was obtained from a single subject. In the practice of the present invention, each data point would typically be identified with the particular subject, as well as the demographic, etc. characteristic of that subject.

Other data attributes will be apparent to persons of ordinary skill in the art in light of the teachings of the present specification.

2.6 STORAGE OF DATA SETS AND ASSOCIATION OF DATA POINTS WITH RELEVANT DATA ATTRIBUTES

A number of formats exist for storing data sets and simultaneously associating related attributes, including but not limited to (1) tabular, (2) relational, and (3) dimensional. In general the databases comprise data points, a numeric value which correspond to physical measurement (an "acquired" datum or data point) or to a single numeric result calculated or derived from one or more acquired data points that are obtained using the various methods disclosed herein. The databases can include raw data or can also include additional related information, for example data tags also referred to as "attributes" of a data point. The databases can take a number of different forms or be structured in a variety of ways.

The most familiar format is tabular, commonly referred to as a spreadsheet (e.g., FIGS. 1, 2, and 3). A variety of spreadsheet programs are currently in existence, and are typically employed in the practice of the present invention, including but not limited to Microsoft Excel spreadsheet software and Corel Quattro spreadsheet software. In this format, association of data points with related attributes occurs by entering a data point and attributes related to that data point in a unique row at the time the analyte measurement occurs.

Further, rational, relational (Database Design for Mere Mortals, by Michael J. Hernandez, 1997, Addison-Wesley Pub. Co., publisher; Database Design for Smarties, by Robert J. Muller, 1999, Morgan Kaufmann Publishers, publisher; Relational Database Design Clearly Explained, by Jan L. Harrington, 1998, Morgan Kaufmann Publishers, publisher) and dimensional (Data-Parallel Computing, by V. B. Muchnick, et al., 1996, International Thomson Publishing, publisher; Understanding Fourth Dimensions, by David Graves, 1993, Computerized Pricing Systems, publisher) database systems and management may be employed as well.

Relational databases typically support a set of operations defined by relational algebra. Such databases typically include tables composed of columns and rows for the data included in the database. Each table of the database has a primary key, which can be any column or set of columns, the values for which uniquely identify the rows in a table. The tables in the database can also include a foreign key that is a column or set of columns, the values of which match the primary key values of another table. Typically, relational databases also support a set of operations (e.g., select, join and combine) that form the basis of the relational algebra governing relations within the database.

Such relational databases can be implemented in various ways. For instance, in Sybase® (Sybase Systems, Emeryville, Calif.) databases, the tables can be physically segregated into different databases. With Oracle® (Oracle Inc., Redwood Shores, Calif.) databases, in contrast, the various tables are not physically separated, because there is one instance of work space with different ownership specified for different tables. In some configurations, databases are all located in a single database (e.g., a data warehouse) on a single computer. In other instances, various databases are split between different computers.

It should be understood, of course, that the databases are not limited to the foregoing arrangements or structures. A variety of other arrangements will be apparent to those of skill in the art.

2.7 DATABASE MANIPULATION TO PRODUCE USEFUL INFORMATION

Databases formulated using the methods of the present invention are useful in that they can be manipulated, for example, using a variety of statistical analyses, to produce useful information. The databases of the present invention may be generated, for example, from data collected for an individual or from a selected group of individuals over a defined period of time (e.g., hours, days, or months), from derived data, and from data attributes.

The present invention further relates to a method for manipulating an analyte data points, derived data, and data attributes database in order to provide a useful result, said method comprising providing an analyte data points, derived data, and data attributes database, and manipulating and/or analyzing the database.

For example, data sets may be aggregated, sorted, selected, sifted, clustered and segregated by means of the attributes associated with the data points. A number of database management systems and data mining software programs exist which may be used to perform the desired manipulations.

Relationships in the database can be directly queried and/or the data analyzed by statistical methods to evaluate the information obtained from manipulating the database.

For example, a distribution curve can be established for a selected data set, and the mean, median and mode calculated therefor. Further, data spread characteristics, e.g. variability, quartiles and standard deviations can be calculated.

The nature of the relationship between a particular variable and analyte levels can be examined by calculating correlation coefficients. Useful methods for doing so include but are not limited to the following: Pearson Product Moment Correlation and Spearman Rank Order Correlation.

Analysis of variance permits testing of differences among sample groups to determine whether a selected variable has a discernible effect on the parameter being measured. For example, the effect of various demographic factors on the efficacy of an experimental drug in normalizing blood glucose levels (efficacy being measured in terms of total glucose excursion) could be analyzed by performing an analysis of variance between two groups which differ only with respect to that particular demographic factor.

Non-parametric tests may be used as a means of testing whether variations between empirical data and experimental expectancies are attributable merely to chance or to the variable or variables being examined. These include the Chi Square test, the Chi Square Goodness of Fit, the 2×2 Contingency Table, the Sign Test, and the Phi Correlation Coefficient.

There are numerous tools and analyses available in standard data mining software that can be applied to the analysis of the databases of the present invention. Such tools and analyses include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory-driven, relationships.

Exemplary data mining software that can be used in analysis and/or generation of the databases of the present invention includes, but is not limited to: Link Analysis (e.g., Associations analysis, Sequential Patterns, Sequential time patterns and Bayes Networks); Classification (e.g., Neural Networks Classification, Bayesian Classification, k-nearest neighbors classification, linear discriminant analysis, Memory based Reasoning, and Classification by Associations); Clustering (e.g., k-Means Clustering, demographic clustering, relational analysis, and Neural Networks Clustering); Statistical methods (e.g., Means, Std dev, Frequencies, Linear Regression, non-linear regression, t-tests, F-test, Chi2 tests, Principal Component Analysis, and Factor Analysis); Prediction (e.g., Neural Networks Prediction Models, Radial Based Functions predictions, Fuzzy logic predictions, Times Series Analysis, and Memory based Reasoning); Operating Systems; and Others (e.g., Parallel Scalability, Simple Query Language functions, and C++ objects generated for applications). Companies that provide such software include, for example, the following: Adaptative Methods Group at UTS (UTS City Campus, Sydney, NSW 2000), CSI®, Inc., (Computer Science Innovations, Inc. Melbourne, Fla.), IBM® (International Business Machines Corporation, Armonk, N.Y.), Oracle® (Oracle Inc., Redwood Shores, Calif.) and SAS® (SAS Institute Inc., Cary, N.C.).

These methods and processes may be applied to the databases of the present invention, for example, databases comprising, analyte data sets, derived data, and data attributes.

For a general discussion of statistical methods applied to data analysis, see Applied Statistics for Science and Industry, by A. Romano, 1977, Allyn and Bacon, publisher.

Some exemplary applications of the present invention are as follows. Databases generated using an analyte monitoring system, e.g. the GlucoWatch biographer, are useful in clinical studies examining drug efficacy in controlling blood glucose levels, and in examining a number of variables which may affect drug efficacy. Further, such databases are useful to individuals to help them understand trends in managing, for example, diabetes. In addition, common risk factors can be identified among selected groups. For example, a database including GlucoWatch biographer data, user inputs, data identifiers, and subject identifiers, could be evaluated to identify whenever multiple hyperglycemic events occurred within a pre-defined time period. Statistical analyses could then be applied to data attributes associated in the database with these values. Significant associations are identified using appropriate statistical methods and may, for example, identify that such multiple hyperglycemic events are most common during the night in men who did not eat a meal or snack before retiring.

Figure 5:
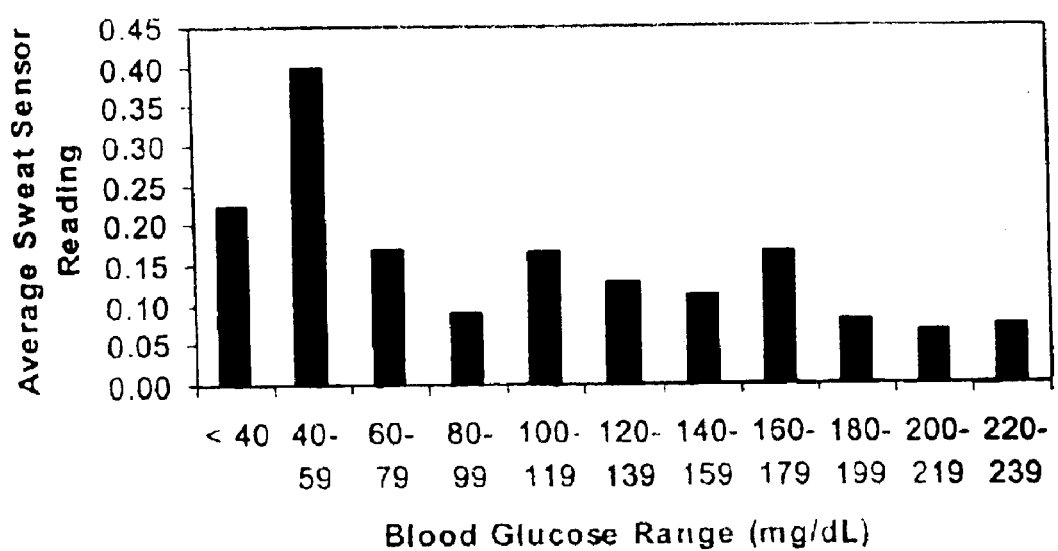
FIG. 5 presents data for average skin conductivity reading vs. blood glucose range.
Figure 6:
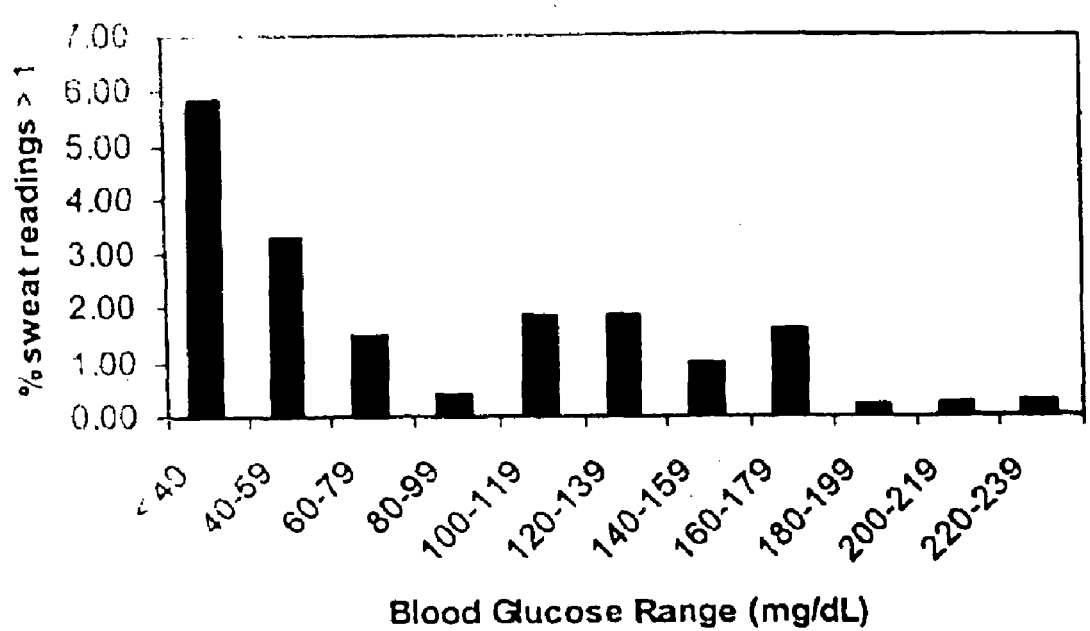
FIG. 6 presents data concerning percentage of skin conductivity readings indicating perspiration vs. blood glucose range.

Several examples of identifying important correlations among parameters in an analyte data points, derived data, and data attributes database generated as described herein are presented in Example 1. For example, analysis of the database provided a correlation between lower average skin temperature and hypoglycemic blood glucose levels (FIG. 4). Accordingly, the results demonstrate that temperature may very well be warranted as a useful parameter to assist in the prediction of hypoglycemia. Further, FIG. 5 shows the average skin conductivity reading for all the measurement cycles within each reference blood glucose range. As can be seen in the figure, the trend was relatively flat over the euglycemic and hypoglycemic ranges. However, the three highest averages occured in the <40 mg/dL, 40–59 mg/dL, and 60–79 mg/dL ranges (i.e., the hypoglycemic region). These results indicated a correlation of a higher degree of perspiration with the hypoglycemic readings. Finally, the data from FIG. 5 were analyzed in a different manner by plotting the percentage of all readings with skin conductivity readings greater than one over the same reference blood glucose ranges (FIG. 6). As can be seen from analysis of the data in FIG. 6, there is a pronounced increase in the percentage of positive perspiration indications in the hypoglycemic regions below 60 mg/dL.

2.8 HARDWARE/SOFTWARE AND SYSTEM CONSIDERATIONS

A. Hardware/Software

Various computer systems, typically comprising one or more microprocessors, can be operably connected to the analyte monitoring system to store, retrieve, and analyze database information. The computer system can be as simple as a stand-alone computer that is not networked to other computers, provided the system has a form of data storage, for example disk drives, removable disk storage, for example ZIP® drives (Iomega Corporation, Roy, Utah), optical medium (e.g., CD-ROM), magnetic tape, solid-state memory, and/or bubble memory. Alternatively, the computer system can include a networked computer system in which a computer is linked to one or more additional computers, for example a network server. The networked system can be an intranet system and/or a system linked to other computers via the Internet. Thus, the computer systems can be Internet-based systems or non-Internet based systems.

In addition, devices such as the Personal Digital Assistants (PDA), for example Palm Pilot™ (Palm Inc., Santa Clara, Calif.) or Handspring™ Visor™ (Handspring, Inc., Mountain View, Calif.) and Pocket PCs (PPC), for example Casio® EM500 Multimedia Cassiopeia Pocket PC (Casio Inc., Dover, N.J.) or Compaq® iPAQ™ (Compaq Computer Corporation, Houston, Tex.) can be operably connected to the analyte monitoring system to store and retrieve patient database information. The PDA or PPC can be a simple stand-alone device that is not networked to other computers, provided the device has a form of data storage, for example solid-state memory, SD (secure digital) and MMC (multimedia card) cards. Alternatively, the PDA or PPC can be attached to a network in which the unit is linked to one or more computers, for example a network server or PC. The networked PDA or PPC can be an intranet system and/or a system linked to computers via the Internet. Thus, the PDA or PPC systems can be Internet attached systems or non-Internet attached systems.

B. Stand-Alone System

Figure 7:
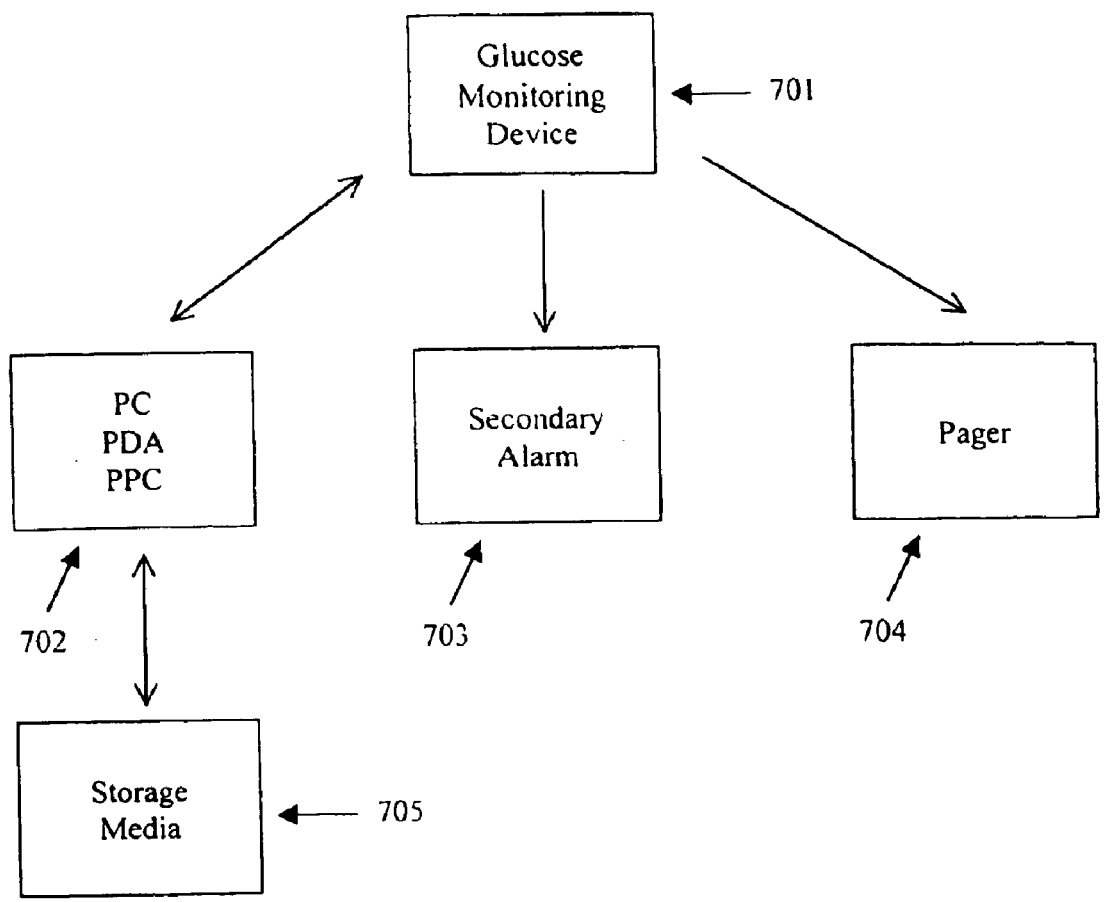
FIG. 7 presents an illustration of a representative stand-alone computer system, PDA or PPC interfaced with a glucose monitor system.

FIG. 7 is an illustration of a representative computer system, PDA or PPC suitable for performing the methods of the present invention; however FIG. 7 depicts but one example of many possible computer types or configurations capable of being used with the present invention (e.g., the GlucoWatch biographer, a glucose monitoring device, used as an example of an analyte monitoring system). The following descriptions of the glucose monitoring device (as an example of an analyte monitoring device) include descriptions of the GlucoWatch biographer (Cygnus, Inc., Redwood City, Calif.) and a similar multi-component version of this device (see, for example, WO 00/47109, published 17 Aug. 2000, herein incorporated by reference). A multi-component device may, for example, comprise two separate portions: one that takes the raw data and transmits it to a second readout device that processes the data, displays it to the user, has basic alarm functions, and serves as the connection to further devices. The basic communications between the sensor and the readout device are sending data to the readout device and sending command's back to the sensor. (These two portions could be combined into a single device comprising all of the functions of the two portions.) Such a readout device can have a number of embodiments. It can be a pager, a watch, a credit-card sized device, a personal digital assistant, a cellular phone, or other device. Several devices can connect to this readout device. The readout device can, for example, communicate to an auxiliary alarm device to provide an enhance alarm (e.g., a louder alarm sound, a synthesized voice alarm, or alarm remote from the readout device). The readout can be connected to a PC in order to, for example, download data to a data analysis program. This connection could be made directly, or via some type of serial interface adapter (as described below).

Connection from the readout device to a central network (e.g., the Internet) can be made either directly, or via serial interface adapter. For example, a direct connection could be made if the readout device had wireless capability; alternately, a connection through a SIA or other sort of docking station between the device and the network.

FIG. 7 depicts a representative stand-alone computer system, PDA or PPC 702 interfaced with a glucose monitor system 701. In some instances, a computer system, PDA or PPC includes a computer having an Intel® Pentium® microprocessor (Intel Corporation, Santa Clara, Calif.) that runs the Microsoft® WINDOWS® Version 3.1, WINDOWS95®, WINDOWS98®, or WINDOWS2000® operating system (Microsoft Corporation, Redmond, Wash.). Of course other microprocessors such as the ATHLON™ microprocessor (Advanced Micro Devices, Inc., Sunnyvale, Calif.) and the Intel® CELERON® and XEON® microprocessors can be utilized. The methods and systems can also include other operating systems, for example, UNIX, LINUX, Apple MAC OS 9 and OS X (Apple, Cupertino, Calif.), PalmOS® (Palm Inc., Santa Clara, Calif.), Windows® CE 2.0 or Windows® CE Professional (Microsoft Corporation, Redmond, Wash.) without departing from the scope of the present invention. Also illustrated in FIG. 7 is the storage media 705, for example disk drive, removable disk storage, CD-ROM, required to store and retrieve patient database information. FIG. 7 illustrates a secondary alarm 703 and pager 704 which can be used with a glucose monitoring device. An exemplary secondary alarm is one that amplifies or transforms the alert/alarm of the analyte monitoring device (e.g., an alert/alarm triggered by an out of range glucose value, a predicted out of range glucose value, or change in glucose levels that exceed a predetermined rate) to be more readily perceived by the user of the analyte monitoring device. Alternately, such a secondary alarm may be placed near a significant other or parent to alert a person other than the user to the alert/alarm. A paging device (e.g., pager, cell phone, etc.) may be used to alert a person other than the user to the alert/alarm, for example, a health care professional or emergency medical support (see, for example, WO 00/47109, published 17 Aug. 2000, herein incorporated by reference).

A glucose monitoring device communicates with a computer system, PDA or PPC using an standard computer interface, for example a serial interface or Universal Serial Bus (USB) port. Alternatively, a glucose monitoring device can communicate with the computer system, PDA or PPC using a standard wireless interface, for example radio frequency (RF) technology—IEEE 802.11 and Bluetooth, and/or infrared technologies. The data can be encoded in the standard manner, for example American Standard Code for Information Interchange (ASCII) format—a standard seven-bit code that was proposed by ANSI in 1963, and finalized in 1968. ASCII is the common code for microcomputer equipment.

The computer system, PDA or PPC can store the information into a database using a wide variety of existing software which provides a means for inputting data points, and associating the data points with data attributes. Available systems for generating databases and manipulating the resulting databases include but are not limited to Excel® (Microsoft® Corporation, Seattle, Wash.) spreadsheet software, Quattro® (Corel Inc., Ottawa, Canada), Sybase® (Sybase Systems, Emeryville, Calif.), Oracle® (Oracle Inc., Redwood Shores, Calif.), and Sagent Design Studio® (Sagent Technologies Inc., Mountain View, Calif.) systems software. Further, statistical packages and systems for data analysis and data mining are also available (see above). Illustrative examples include but are not limited to SAS® (SAS Institute Inc., Cary, N.C.) and SPSS® (SPSS Inc., Chicago, Ill.). The database can be recorded on, for example a disk drive—internal or external to the system, a Read/Write CD-ROM drive, a tape storage system, solid-state memory or bubble memory, an SD or MMC. In addition to saving the data in a database, a glucose monitoring device and/or computer system, PDA or PPC can forward the information to an auxiliary readout device such as a secondary alarm, pager, cellular phone, or other display monitor.

Alternatively, the computer system, PDA or PPC can communicate with a glucose monitoring device using the same wired or wireless interface, for example to update the software running on a glucose monitoring device or provide feedback to the user based upon an analysis run on the computer system, PDA or PPC which requires data not available on a glucose monitoring device.

C. Networked System

Figure 8:
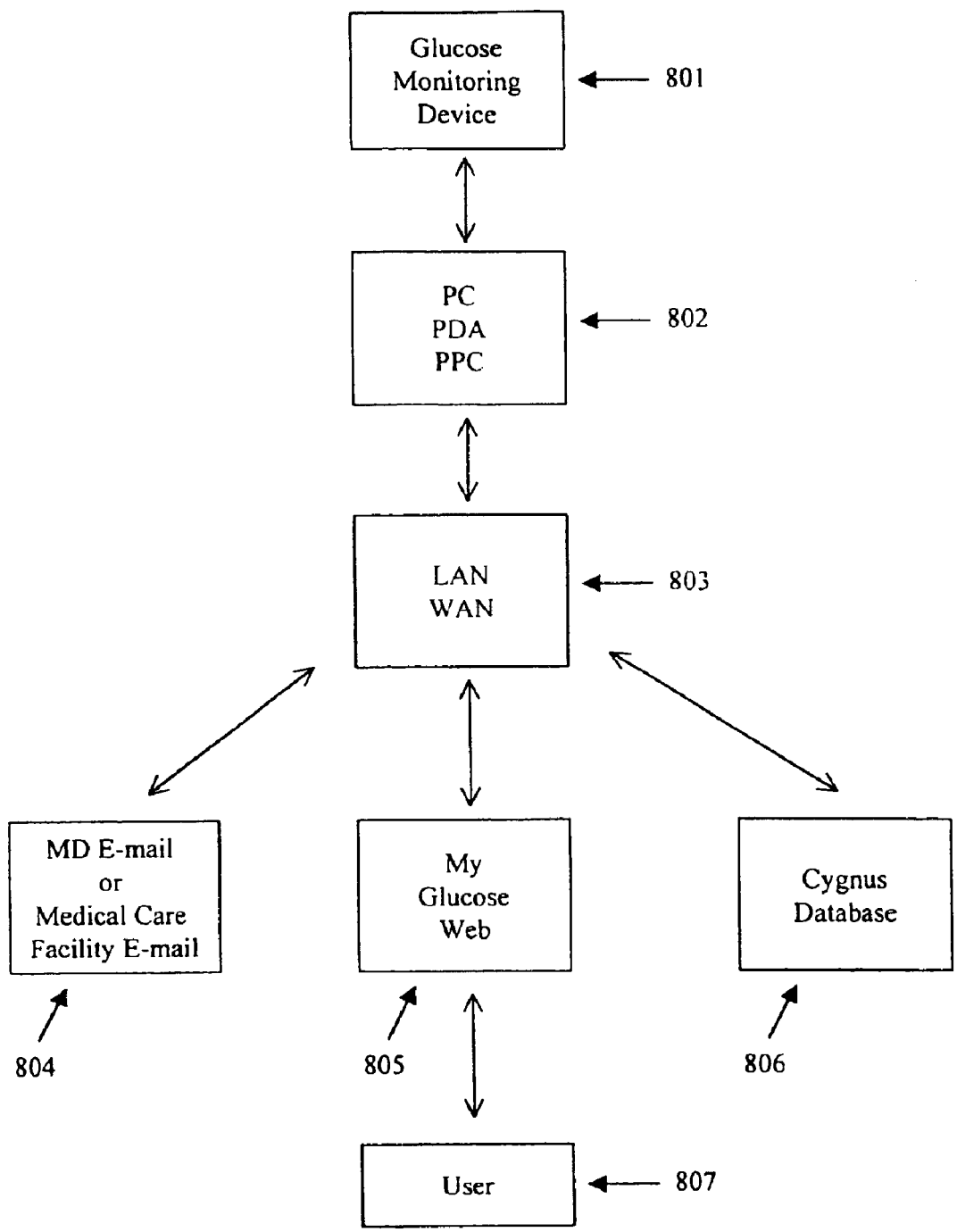
FIG. 8 presents an illustration of a representative networked computer system, PDA or PPC suitable for performing the methods of the present invention.

FIG. 8 is an illustration of a representative networked computer system, PDA or PPC suitable for performing the methods of the present invention; however FIG. 8 depicts but one example of many possible networked computer types or configurations capable of being used with the present invention. FIG. 8 depicts a representative networked computer system, PDA or PPC 802 operably interfaced with a glucose monitoring device 801. The networked computer system, PDA or PPC can interface with a glucose monitoring device in a similar manner as the stand-alone computer system, PDA or PPC. Further illustrated in FIG. 8, the computer system, PDA or PPC can be connected to a number of network systems, for example a local area network (LAN) or a wide area network (WAN) 803. The network computer system, PDA or PPC includes the necessary functionality for forwarding the data in established formats, for example Ethernet or Token Ring Packets or Frames, HTML-formatted data, or WAN digital or analog protocols, in combination with any parameter information, for example Destination Address, or Cyclic Redundancy Check (CRC). CRC is a powerful and-easily implemented technique to obtain data reliability. The CRC technique is used to protect blocks of data called Frames. Using this technique, the transmitter appends an extra n-bit sequence to every frame called Frame Check Sequence (FCS). The FCS holds redundant information about the frame that helps the transmitter detect errors in the frame. The CRC is one of the most used techniques for error detection in data communications into a format suitable for transmission across a transmission line for delivery to a database server. One example of such a data integrity check is shown in Column 7 of FIG. 3 (CHECK SUM). Further, the network system may comprises the necessary software and hardware to receive the data from the readout device, store the data, process the data, display the data in a variety of ways, and communicate back to the readout device as well as to allow communication among a variety of users and between these users to the readout device.

The networked computer system, PDA or PPC can be connected to, for example an Ethernet, Token Ring or FDDI network, using a standard network interface card (NIC), for example a 3Com® EtherLink® NIC (3Com, Inc, Santa Clara, Calif.) which provide network connections over UTP, coaxial, or fiber-optic cabling or an Intel® PRO/100 S Desktop Adapter (Intel Corporation, Santa Clara, Calif.). The networked computer system, PDA or PPC can be connected to a LAN using a standard remote access technology, for example a modem using a plain old telephone system (POTS) line, or a xDSL router connected to a digital subscriber lines (DSL), or a cable modem. Additionally, the networked computer system, PDA or PPC can be connected to the LAN using a standard wireless interface, for example radio frequency (RF) technology—IEEE 802.11 and Bluetooth.

The networked computer system, PDA or PPC would have the same capability of storing data, as the stand-alone system, from a glucose monitoring device onto a storage media, for example a disk drive, tape storage, or CD-ROM. Alternatively FIG. 8 illustrates, the networked computer system, PDA or PPC 802 would be able to transfer data to any device connected to the networked computer system, PDA or PPC, for example a medical doctor or medical care facility using standard e-mail software 804, a central database using database query and update software 806 (e.g., a data warehouse of data points, derived data, and data attributes obtained from a large number of users using GlucoWatch biographer, where the data warehouse is maintained by Cygnus, Inc., the manufacturer of the biographer), and/or the user's personal database 805 (e.g., the personal database of a user of a GlucoWatch biographer, designated in the figure as "My GlucoWatch Website"). Alternatively, the user 807 could access their "My GlucoWatch Website" 805 from a doctor's office or medical facility, using any computer system with Internet access, to review historical data which may be useful for determining treatment. When a glucose monitoring device is connected to a networked computer system, PDA or PPC, it has the capability to store or retrieve data from any appropriate database worldwide.

If the networked computer system, PDA or PPC on the LAN includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as may be necessary if the database server is distributed over two or more different computers.

Usually each networked computer system, PDA or PPC includes a World Wide Web browser that provides a user interface to the networked database server. The networked computer system, PDA or PPC is able to construct search requests for retrieving information from a database via a Web browser. With access to a Web browser users can typically point and click to user interface elements such as buttons, pull down menus, and other graphical user interface elements to prepare and submit a query that extracts the relevant information from the database. Requests formulated in this manner are subsequently transmitted to the Web application that formats the requests to produce a query that can be used to extract the relevant information from the database.

When Web-based applications are utilized, the Web application accesses data from a database by constructing a query in a database language such as Sybase or Oracle SQL which is then transferred to a relational database management system that in turn processes the query to obtain the pertinent information from the database.

Accordingly, in one aspect the present invention describes a method of connecting a glucose monitoring device to a computer, a PDA, a network, for example the Internet, and methods of using this connection to provide real-time and delayed data analysis, alert functions, and device and troubleshooting and servicing functions. The central network can also allow access by the physician to a subject's data. Similarly, an alert could be sent to the physician if a subject's readings are out of a predetermined range, etc. The physician can then send advice back to the patient via e-mail or a message on a web page interface (e.g. "My GlucoWatch"). Also, the central network can provide a way for the manufacturer of an analyte monitoring device to communicate to a user of the device and/or the device itself. For example, troubleshooting of the analyte monitoring device can be facilitated by interrogating the device through the network. Software updates can be downloaded into the device from the manufacturer as well. Entering codes to ensure that a user has been trained in correct usage of the device can also be done. Further, access to the entire database of data from all users of an analyte monitoring device may be useful to the manufacturer (and others) for statistical or research purposes. Appropriate network security features (e.g., for data transfer, inquiries, device updates, etc.) are of course employed.

In addition, because the analyte monitoring device is uploading data continually, frequently, or periodically to the central network, near real-time feedback can be provided to a user in the form of alerts, for example, if readings are outside of a predetermined range, or the device seems to be malfunctioning. Advanced trend analysis software can be incorporated into the central network that can activate alerts to the user (e.g., if post-meal glucose readings are out of control). Delayed alerts or suggestions can also be delivered to the user daily or at frequencies determined by the uploading frequency of the analyte monitoring device.

In the context of a glucose monitoring device providing frequent glucose measurements (e.g., the GlucoWatch biographer or similar device), one advantage of network conductivity is that the data can be streamed to the network in real time and is sufficiently dense to allow decisions to be made by software at the central network based on this data stream. Such decisions may be communicated to the user, as well as to other persons, such as a medical care professional. Decisions, such as suggestions on insulin dosage, caloric intake/output, etc., are difficult to make accurately without such large amounts of data as provided by the methods and devices of the present invention.

D. Graphical User Interface

In certain of the computer systems, an interface such as an interface screen that includes a suite of functions is included to enable users to easily access the information they seek from the databases of the invention. Such interfaces usually include a main menu page from which a user can initiate a variety of different types of analyses (such as discussed above, for example, initiate a search for hypoglycemic events and related attributes, followed by initiating a selected analysis to identify salient factors). For example, the main menu page for the databases generally include buttons for accessing certain types of information, including, but not limited to, project information, inter-project comparisons, times of day, events, dates, times, ranges of analyte values, etc.

An exemplary main user interface between the user of the analyte monitoring device (the subject) and the central network system may be a personal, customized Web page (e.g., "My GlucoWatch" discussed above). This Web page can enable the patient to access all the data uploaded from the device to the central network and a variety of user-friendly forms to allow the patient to analyze the data and draw useful conclusions. The web page can also, for example, flag hypoglycemic events, hyperglycemic events, etc.

E. Computer Program Products

A variety of computer program products can be utilized for conducting the various methods and analyses disclosed herein. In general, the computer program products comprise a computer-readable medium and the code necessary to perform the methods set forth supra. The computer-readable medium on which the program instructions are encoded can be any of a variety of known medium types, including, but not limited to, microprocessors, floppy disks, hard drives, ZIP drives, WORM drives, magnetic tape and optical medium such as CD-ROMs.

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

TEMPERATURE AND PERSPIRATION AS INDICATORS OF HYPOGLYCEMIA

Several researchers have investigated the correlation between skin temperature and perspiration and the presence of hypoglycemia. Bolinger, et al. (Bolinger, R. E., et al., *Diabetes,* 13, 600–605 (1964)) reported that a decrease in skin resistance, indicating the onset of perspiration, coincided with the onset of hypoglycemic symptoms. Levandoski, et al. (Levandoski, L. A., et al., in *Artificial Systems for Insulin Delivery,* P. Brunetti, et al., Eds. Raven Press: New York (1983), p. 353–356) evaluated a then-commercially available device, the Teledyne Sleep Sentry® device which uses both skin conductivity and temperature to detect nocturnal hypoglycemia. In a study of insulin-induced hypoglycemia in 27 diabetic patients, the device correctly detected the hypoglycemia 80% of the time. In widespread use, however, the Sleep Sentry device demonstrated a high rate of false positive alarms, and was not a commercial success, and is not currently on the market.

Preliminary tests of the correlation between skin temperature and skin conductivity, and hypoglycemic blood glucose levels were performed on data from one clinical trial. Temperature and perspiration data from the GlucoWatch biographer have been analyzed for a total of 213 GlucoWatch biographer applications on 121 diabetic subjects. This data set consisted of the temperature, perspiration measurement and reference blood glucose value for 5346 GlucoWatch biographer measurement cycles. For this trial, the subjects were tested in a clinical setting, but allowed to walk around, etc, thus simulating a home environment.

In order to determine whether a correlation existed between skin temperature and perspiration, and hypoglycemia, the data were sorted into reference blood glucose range bins from <40 mg/dL to 240 mg/dL. The minimum skin temperature for each measurement cycle in each bin was averaged and plotted in FIG. 4. As can be seen, the skin temperature as measured by the GlucoWatch biographer was lower than average when the reference blood glucose was lower than 120 mg/dL, and was lowest when the blood glucose was in the lowest hypoglycemic range. This preliminary result demonstrated a correlation between lower average skin temperature and hypoglycemic blood glucose levels. Accordingly, the results demonstrate that temperature may very well be warranted as a useful parameter to assist in the prediction of hypoglycemia.

The data from the skin conductivity sensor on the GlucoWatch biographer was plotted in a similar manner. The GlucoWatch biogrpher skin conductivity measurements were converted to an arbitrary scale from 0–10. For data integrity screening purposes, skin conductivity readings above 1 were considered an indication of perspiration occuring. FIG. 5 shows the average skin conductivity reading for all the measurement cycles within each reference blood glucose range. The trend was relatively flat over the euglycemic and hyperglycemic ranges with the three highest averages occuring in the <40 mg/dL, 40–59 mg/dL, and 60–79 mg/dL ranges in the hypoglycemic region, indicating a higher degree of perspiration in the hypoglycemic region.

These data were presented in a different manner (FIG. 6) by plotting the percentage of all readings with skin conductivity readings greater than one (therefore, above the a priori determined perspiration threshold) over the same reference blood glucose ranges. As can be seen from the data, there is a pronounced increase in the percentage of positive perspiration indications in the hypoglycemic regions below 60 mg/dL.

These analyses demonstrate some aspects of the usefulness of the databases and methods of the present invention.

Although preferred embodiments of the subject invention have been described in some detail, it is understood that obvious variations can be made without departing from the spirit and the scope of the invention as defined by the appended claims.

What is claimed is:

1. A method of formulating one or more analyte data databases, said method comprising:

collecting analyte measurement values from one or more subject using an analyte monitoring device, comprising a sensing device, for each subject, and said analyte monitoring device providing (i) frequent analyte measurement values, wherein said analyte measurement values comprise acquired data points that are specifically related to analyte amount or concentration in she subject, (ii) one or more data attributes, and (iii) one or more error messages related to skipped analyte measurement values; and formulating said one or more analyte data databases by associating each of said data points and each of said one or more error messages related to skipped analyte measurement values with one or more data attributes.

2. The method of claim 1, wherein said data points further comprise derived data determined from one or more acquired data points and the derived data are associated with the data points from which they are derived.

3. The method of claim 2, wherein each of said derived data are associated with one or more data attributes.

4. The method of claim 2, wherein said analyte is glucose and said derived data comprises glucose amount or concentration.

5. The method of claim 4, wherein said analyte monitoring device is a glucose monitoring device, said glucose monitoring device comprising a sensing device, a display, and means to provide an audible alert when glucose levels in a subject being monitored are outside of a predetermined range.

6. The method of claim 1, wherein said analyte measurement values are collected from a single individual.

7. The method of claim 1, wherein said analyte measurement values are collected from more than one individual.

8. The method of claim 7, wherein said formulating further comprises compiling multiple databases from each database where the data points are collected from a single individual and the data points for each single individual are associated with one or more relevant data attributes.

9. The method of claim 1, wherein said analyte is a biological analyte.

10. The method of claim 9, wherein said biological analyte is glucose.

11. The method of claim 1, wherein said acquired data points comprise electrochemical signals.

12. The method of claim 11, wherein said data attributes are selected from the group consisting of: chronological information, user perspiration levels, device operating temperature, missed measurements; skipped measurements, user body temperature, user skin conductance, environmental variables, alarm events, activity codes, total excursion, mean value, statistical function, subject code, demographic information, physical characteristics, and disease-associated characteristics.

13. The method of claim 1, wherein said analyte monitoring device is capable of measuring more than one analyte.

14. The method of claim 13, wherein one of said analytes is glucose.

15. The method of claim 1, wherein one or more of said analyte measurement values, one or more of said error messages, and one or more of said data attributes are transferred to a server via a network.

16. The method of claim 15, wherein said formulating is carried out on said server.

17. The method of claim 15, wherein said server communicates with said analyte monitoring device.

18. The method of claim 1, wherein said one or more data attributes associated with said data point or said skipped measurement value is one or more data attribute provided by the analyte monitoring device.

19. The method of claim 18, wherein said one or more data attributes are selected from the group consisting of chronological information, user perspiration level, device operating temperature, user body temperature, user skin conductance, environmental variable, number of alarm events, and type of alarm events.

20. The method of claim 1, wherein said one or more data attributes associated with said data point or said skipped measurement value is one or more data attribute comprising a user input.

21. The method of claim 20, wherein said one or more data attributes are selected from the group consisting of activity codes, sleep and administration of medications, dose of medications, and times of medications.

22. The method of claim 1, wherein said one or more data attributes associated with said data point or said skipped measurement value is one or more data identifier.

23. The method of claim 22, wherein said one or more data identifiers is selected from the group consisting of maximum analyte values, minimum analyte values, hypoglycemic analyte values, and hyperglycemic analyte values.

24. The method of claim 1, wherein said one or more data attributes associated with said data point or said skipped measurement value is one or more subject identifier.

25. The method of claim 24, wherein said one or more subject identifiers is selected from the group consisting of a subject code, demographic information, physical characteristic, selected aspects of the subject's medical history, and disease-associated characteristics.

26. One or more analyte data databases on a computer readable medium, comprising
data points collected using an analyte monitoring device, comprising a sensing device, wherein said analyte monitoring device provides (i) frequent analyte measurement values and said analyte measurement values comprise data points that are specifically related to analyte amount or concentration, and (ii) one or more data attributes;
one or more data attributes; and
one or more error messages related to skipped analyte measurement values, wherein the data points and each of said one or more error messages related to skipped analyte measurement values are associated with one or more relevant data attributes.

27. The one or more databases of claim 26, wherein said data points further comprise derived data determined from one or more acquired data points and the derived data are associated with the data points from which they are derived.

28. The one or more databases of claim 27, wherein each of said derived data are associated with one or more data attributes.

29. The one or more databases of claim 27, wherein said analyte is glucose and said derived data comprises glucose amount or concentration.

30. The one or more databases of claim 26, wherein said analyte measurement values are collected from a single individual.

31. The one or more databases of claim 26, wherein said analyte measurement values are collected from more than one individual.

32. The one or more databases of claim 26, wherein said analyte is a biological analyte.

33. The one or more databases of claim 32, wherein said biological analyte is glucose.

34. The one or more databases of claim 26, wherein said acquired data points comprise electrochemical signals.

35. The one or more databases of claim 34, wherein said data attributes are selected from the group consisting of: chronological information, user perspiration levels, device operating temperature, missed measurements; skipped measurements, user body temperature, user skin conductance, environmental variables, alarm events, activity codes, total excursion, mean value, statistical function, subject code, demographic information, physical characteristics, and disease-associated characteristics.

36. The one or more databases of claim 26, wherein said analyte measurement values comprise analyte measurement values for more than one analyte.

37. The one or more databases of claim 36, wherein one of said analytes is glucose.

38. A method of manipulating one or more analyte data databases, comprising
providing the one or more analyte data databases of claim 26; and
manipulating said data points via said attributes associated with said data points to determine relationships between said data points and said attributes.

39. The method of claim 38, wherein said one or more analyte databases are located on a network database server.

40. The method of claim 39, wherein said manipulating is carried out on said network database server.

41. A method of manipulating one or more analyte data databases, comprising
providing the one or more analyte data databases of claim 26; and
manipulating said attributes via said data points associated with said attributes to determine relationships between said attributes and said data points.

42. The method of claim 41, wherein said one or more analyte databases are located on a network database server.

43. The method of claim 42, wherein said manipulating is carried out on said network database server.

44. The one or more databases of claim 26, wherein said one or more data attributes associated with said data point or said skipped measurement value is one or more data attribute provided by the analyte monitoring device.

45. The one or more databases of claim 44, wherein said one or more data attributes are selected from the group consisting of chronological information, user perspiration level, device operating temperature, user body temperature, user skin conductance, environmental variable, number of alarm events, and type of alarm events.

46. The one or more databases of claim 26, wherein said one or more data attributes associated with said data point or said skipped measurement value is one or more data attribute comprising a user input.

47. The one or more databases of claim 46, wherein said one or more data attributes are selected from the group consisting of activity codes, sleep and administration of medications, dose of medications, and times of medications.

48. The one or more databases of claim 26, wherein said one or more data attributes associated with said data point or said skipped measurement value is one or more data identifier.

49. The one or more databases of claim 48, wherein said one or more data identifiers is selected from the group consisting of maximum analyte values, minimum analyte values, hypoglycemic analyte values, and hyperglycemic analyte values.

50. The one or more databases of claim 26, wherein said one or more data attributes associated with said data point or said skipped measurement value is one or more subject identifier.

51. The one or more databases of claim 50, wherein said one or more subject identifiers is selected from the group consisting of a subject code, demographic information, physical characteristic, selected aspects of the subject's medical history, and disease-associated characteristics.

* * * * *